(12) United States Patent
Pak et al.

(10) Patent No.: US 12,364,510 B2
(45) Date of Patent: Jul. 22, 2025

(54) QUICK RELEASE MECHANISM FOR STRUT

(71) Applicant: Stryker European Operations Limited, Carrigtwohill (IE)

(72) Inventors: Chulho Pak, Mahwah, NJ (US); Subash K. Mannanal, Mahwah, NJ (US)

(73) Assignee: Stryker European Operations Limited, Carrigtwohill (IE)

( * ) Notice: Subject to any disclaimer, the term of this patent is extended or adjusted under 35 U.S.C. 154(b) by 388 days.

(21) Appl. No.: 18/057,901

(22) Filed: Nov. 22, 2022

(65) Prior Publication Data
US 2023/0193936 A1    Jun. 22, 2023

Related U.S. Application Data

(60) Provisional application No. 63/291,490, filed on Dec. 20, 2021.

(51) Int. Cl.
*A61B 17/66* (2006.01)
*A61B 17/62* (2006.01)

(52) U.S. Cl.
CPC .............. *A61B 17/66* (2013.01); *A61B 17/62* (2013.01)

(58) Field of Classification Search
CPC ....... A61B 17/64; A61B 17/645; A61B 17/66; A61B 17/62; F16B 7/0406
See application file for complete search history.

(56) References Cited

U.S. PATENT DOCUMENTS

| | | | |
|---|---|---|---|
| 6,030,386 A * | 2/2000 | Taylor | A61B 17/62 606/56 |
| 8,057,474 B2 | 11/2011 | Knuchel | |
| 8,574,232 B1 | 11/2013 | Ross | |
| 8,864,763 B2 | 10/2014 | Murray | |
| 8,932,358 B1 * | 1/2015 | Nehls | A61F 2/4455 623/17.16 |
| 9,101,398 B2 | 8/2015 | Singh | |
| 10,010,350 B2 | 7/2018 | Mannanal | |
| 2005/0113921 A1 * | 5/2005 | An | A61F 2/44 623/17.11 |
| 2010/0312243 A1 * | 12/2010 | Ross | A61B 17/64 606/56 |

(Continued)

FOREIGN PATENT DOCUMENTS

WO    2020047334    3/2020

*Primary Examiner* — Julianna N Harvey
(74) *Attorney, Agent, or Firm* — SLEMAN & LUND LLP

(57) ABSTRACT

An adjustable length strut for use in an external fixation system may include an outer tube, an inner tube within the outer tube, and a first adjustment knob. A plurality of texturized surfaces may extend in the length direction of the inner tube, each of the plurality of texturized surfaces of the inner tube being spaced apart from each other in the circumferential direction of the inner tube. Each circumferentially adjacent pair of texturized surfaces of the inner tube is separated by a non-texturized surface. The first adjustment knob may also include texturized surfaces separated by non-texturized surfaces, and may be rotatable relative to the outer tube and the inner tube between a locked condition and an unlocked condition. In the locked condition, the texturized surfaces engage each other, to prevent translation of the inner tube relative to the outer tube.

20 Claims, 25 Drawing Sheets

(56) References Cited

U.S. PATENT DOCUMENTS

| | | | |
|---|---|---|---|
| 2011/0208187 A1* | 8/2011 | Wong | A61B 17/6416 |
| | | | 606/56 |
| 2015/0080892 A1* | 3/2015 | Lehmann | A61B 17/66 |
| | | | 606/57 |
| 2016/0022314 A1* | 1/2016 | Bordeaux | A61B 17/66 |
| | | | 606/56 |
| 2018/0132898 A1* | 5/2018 | Cresina | A61B 17/66 |
| 2018/0368887 A1* | 12/2018 | Lauf | A61B 17/62 |
| 2019/0125407 A1* | 5/2019 | Lauf | A61B 17/62 |
| 2019/0282274 A1* | 9/2019 | Singh | A61H 3/00 |
| 2020/0054360 A1* | 2/2020 | Wigginton | A61B 17/66 |
| 2021/0244442 A1* | 8/2021 | Mullaney | A61B 17/62 |
| 2021/0330357 A1* | 10/2021 | Lavoritano | A61B 17/62 |
| 2022/0133357 A1* | 5/2022 | Mullaney | A61B 17/6425 |
| | | | 606/55 |
| 2024/0058037 A1* | 2/2024 | Meiggs | A61B 17/6466 |

* cited by examiner

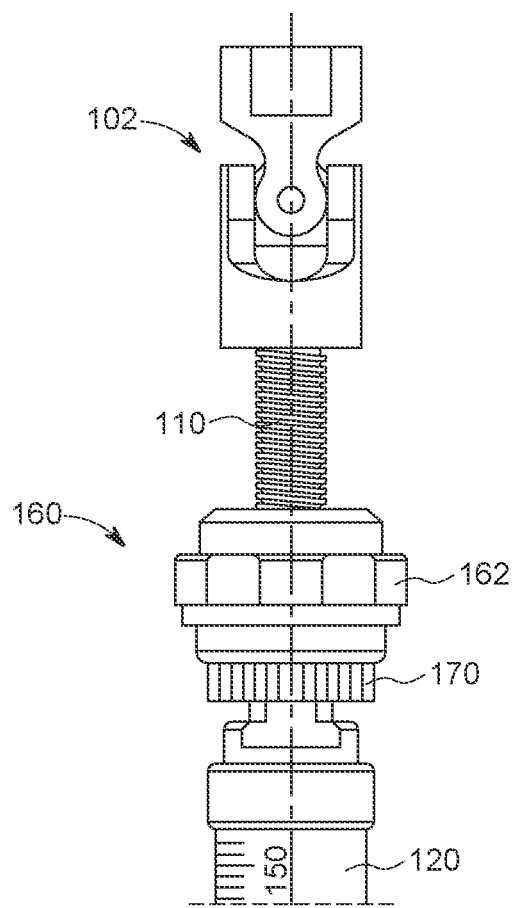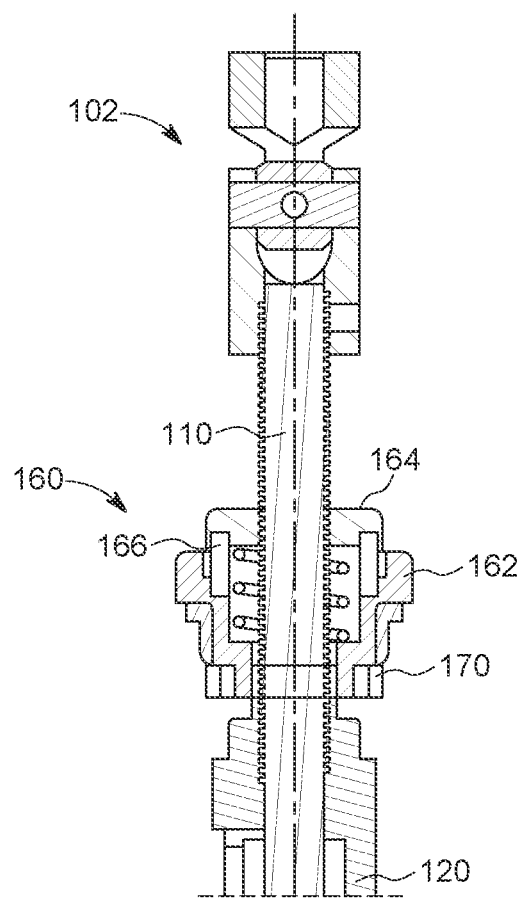
FIG. 8C
FIG. 8D

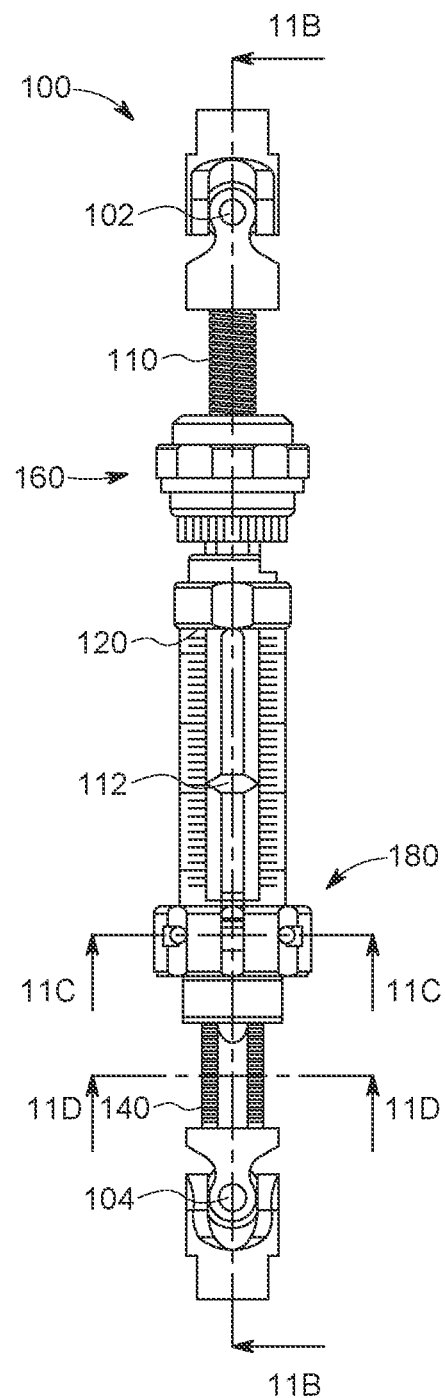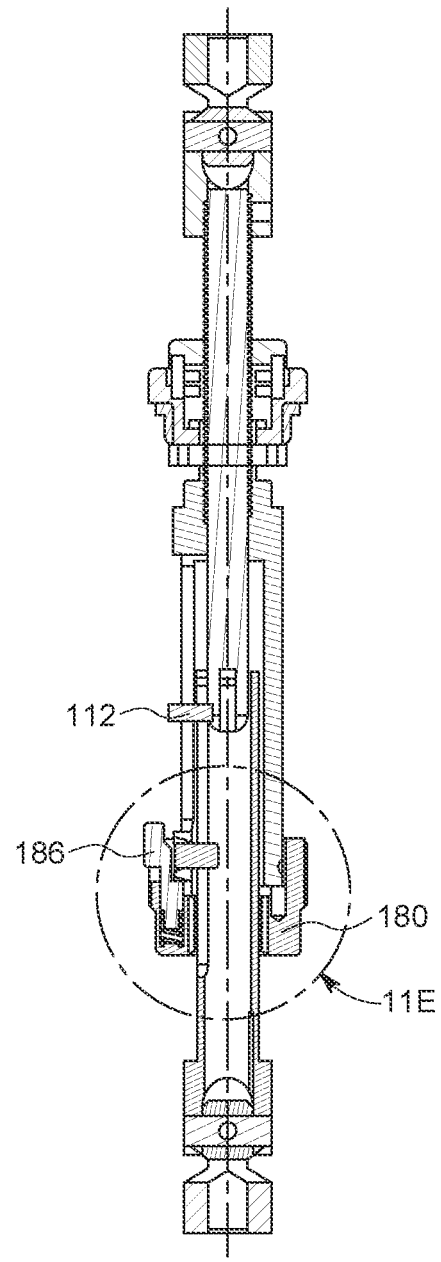
FIG. 11A
FIG. 11B

QUICK RELEASE MECHANISM FOR STRUT

CROSS-REFERENCE TO RELATED APPLICATIONS

This application claims priority to the filing date of U.S. Provisional Patent Application No. 63/291,490, filed Dec. 20, 2021, the disclosure of which is hereby incorporated by reference herein.

BACKGROUND OF THE DISCLOSURE

The disclosure relates to a telescopic strut for an external fixator, especially for use with an external ring fixator.

A plurality of compression-distraction apparatus has been designed and improved by Ilizarov and his group using two external rings to be placed around the limb to be fixed. There are usually at least two such rings, one proximal and one distal ring, which are connected with a plurality of struts or rods. Preferably, these struts are linked to the rings in a way that the attachment points can be pivoted and the length of the strut can be varied to enable adjustment of the external fixation rings.

It may be desirable for such telescopic struts to have the ability to gradually change length during the correction phase, and to also be able to rapidly change length during the assembly/implantation phase. This rapid length change may reduce the time necessary for each strut to be set to the initial length desired for connection to the fixator rings. However, it is important that the rapid length adjustment mode is not unintentionally activated during the correction phase in which strut lengths are to be gradually adjusted. Thus, it would be preferable for the struts to have mechanisms to change between a rapid length adjustment mode and a gradual length adjustment mode quickly and reliably.

BRIEF SUMMARY

According to an aspect of the disclosure, an adjustable length strut is for use in an external fixation system. The strut includes a generally hollow outer tube extending between a first end and a second end. The strut also includes an inner tube sized to fit within and translate relative to the outer tube. The inner tube extends in a length direction and has a circumferential direction. A plurality of texturized surfaces extends in the length direction of the inner tube, each of the plurality of texturized surfaces of the inner tube being spaced apart from each other in the circumferential direction of the inner tube. Each circumferentially adjacent pair of texturized surfaces of the inner tube is separated by a non-texturized surface. The strut also includes a first adjustment knob coupled to the second end of the outer tube. The first adjustment knob has an interior surface defining a channel, the interior surface extending in a length direction and having a circumferential direction. The inner tube passes through the channel. The interior surface has a plurality of texturized surfaces extending in the length direction of the interior surface. Each of the plurality of texturized surfaces of the interior surface is spaced apart from each other in the circumferential direction of the interior surface and each circumferentially adjacent pair of texturized surfaces of the interior surface is separated by a non-texturized surface. The first adjustment knob is rotatable relative to the outer tube and the inner tube between a locked condition and an unlocked condition. In the locked condition, the plurality of texturized surfaces of the inner tube engages the plurality of texturized surfaces of the interior surface of the first adjustment knob to prevent translation of the inner tube relative to the outer tube. In the unlocked condition, the plurality of texturized surfaces of the inner tube aligns with the plurality of non-texturized surfaces of the interior surface of the first adjustment knob to allow translation of the inner tube relative to the outer tube.

The strut may include a threaded rod, the inner tube may be generally hollow, and the threaded rod is sized to fit within the inner tube. The threaded rod may pass through the first end of the outer tube. The strut may include a first joint coupled to an end of the threaded rod, and a second joint coupled to an end of the inner tube, the first joint configured to couple to a first fixation ring of the external fixation system and the second joint configured to couple to a second fixation ring of the external fixation system. The strut may include a second adjustment knob coupled to the first end of the outer tube so that the second adjustment knob is translationally fixed to the outer tube. The threaded rod may pass through an aperture of the second adjustment knob. The second adjustment knob may include internal threading at the aperture configured to engage external threading of the threaded rod, so that rotation of the second adjustment knob relative to the threaded rod causes the threaded rod to translate into or out of the outer tube. The outer tube may include an outer tube slot, and the threaded rod may include a protrusion extending through the outer tube slot, the protrusion being rotatable relative to the threaded rod. An outer surface of the second end of the outer tube may include a circumferential recess. The first adjustment knob may include a first pin passing through the first adjustment knob, the first pin extending transverse the length direction of the interior surface of the first adjustment knob and being at least partially seated in the circumferential recess. The first pin may prevent translational movement of the first adjustment knob relative to the outer tube. The first adjustment knob may include a second pin passing through the first adjustment knob, the second pin extending parallel to the first pin, the channel of the first adjustment knob being positioned between the first pin and the second pin, the second pin being at least partially seated in the circumferential recess.

The strut may include a quick-release pin and spring both at least partially received within the first adjustment knob, the quick release pin including a shoulder extending toward the second end the outer tube. The second end of the outer tube may include a first detent circumferentially spaced from a second detent. When the shoulder of the quick-release pin is received within the first detent, the first adjustment knob may be in the locked condition, and when the shoulder of the quick-release pin is received within the second detent, the first adjustment knob may be in the unlocked condition. The spring may bias the shoulder into the first detent when the first adjustment knob is in the locked condition, and the spring may bias the shoulder into the second detent when the first adjustment knob is in the unlocked condition, the spring bias tending to prevent rotation of the first adjustment knob relative to the outer tube in the absence of applied forces. The second end of the outer tube may include an arcuate recess positioned generally diametrically opposed to the first detent and the second detent. The strut may include a rotation limiting pin at least partially received within the first adjustment knob, a terminal end of the rotation limiting pin extending into the arcuate recess. The arcuate recess may be bounded by a first limiting surface and a second limiting surface, and contact between the rotation limiting pin and the first and second limiting surfaces may define the extent to which the first adjustment knob is capable of rotation relative to the outer tube. When the terminal end of the rotation limiting pin is in contact with the first limiting surface, the shoulder of the quick-release pin may be received within the first detent and the first adjustment knob is in the locked condition, and when the terminal end of the rotation limiting pin is in contact with the second limiting surface, the shoulder of the quick-release pin may be received within the second detent and the first adjustment knob is in the unlocked condition. The plurality of texturized surfaces of the inner tube may include threads extending in the circumferential direction, and at least one of the threads of the inner tube may include a guide thread extending therefrom. The guide thread may be configured to guide the threads of the inner tube into engagement with corresponding threads of the plurality of texturized surfaces of the interior surface of the first adjustment knob as the first adjustment knob is rotated from the unlocked condition to the locked condition.

BRIEF DESCRIPTION OF THE DRAWINGS

FIG. 8C is a side view of the gradual correction knob of FIGS. 8A-8B.

FIG. 8D is a cross-section of the view of FIG. 8C.

FIG. 11A is a side view of the strut of FIG. 5.

FIG. 11B is a cross-section of the strut of FIG. 11A taken along section line 11B-11B of FIG. 11A.

DETAILED DESCRIPTION

Figure 1:
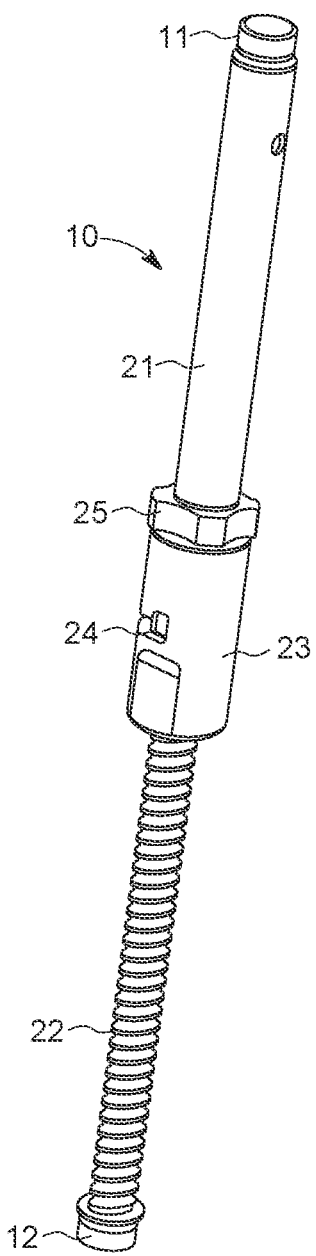
FIG. 1 is a perspective view of a telescopic strut according to the prior art.

Referring to FIG. 1 there is shown a perspective view of a telescopic strut according to the prior art generally denoted as 10. The telescopic strut comprises two free ends 11 and 12 being attachment points for connecting the rod with two external rings to be placed around the limb to be fixed. The attachment points 11 and 12 according to this embodiment comprise cylindrical knobs, but this entirely depends on the kind of fixation element for which the rod is used.

Figure 2:
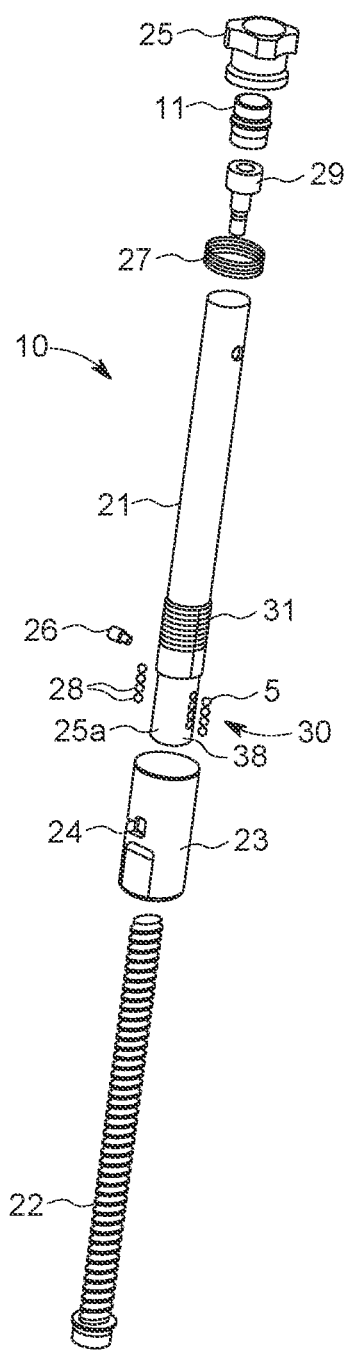
FIG. 2 is an exploded view of the telescopic strut of FIG. 1.

FIG. 1 shows the main components of the telescopic strut. There is an outer tube 21 in which the threaded rod 22 is partially located. The opposite thread 30 is located within the sleeve 23 and is better seen in FIG. 2 as well as FIG. 3 and will be described below. In the illustrated embodiment sleeve 23 comprises a bayonet groove 24 for a quick change between the desired quick length change mode and the fine adjustment mode. The sleeve 23 can be switched between two rotational positions for this, i.e. to lock and unlock the axial direction. Therefore the groove 24 has a U-form, the ends of the groove 24 defining the two positions with the help of a bolt 26 provided within the groove 24. The ends of the groove 24 are oriented in axial direction of the telescopic strut. The ends show in the same direction, towards the spring 27 as can be seen in the exploded view of FIG. 2, to allow displacement of the bolt 26 against the force of said spring 27.

A security mechanism, to avoid unintentional switching, is realized by an additional nut 25, blocking the bolt 26 in one of the free ends of groove 24.

Figure 3:
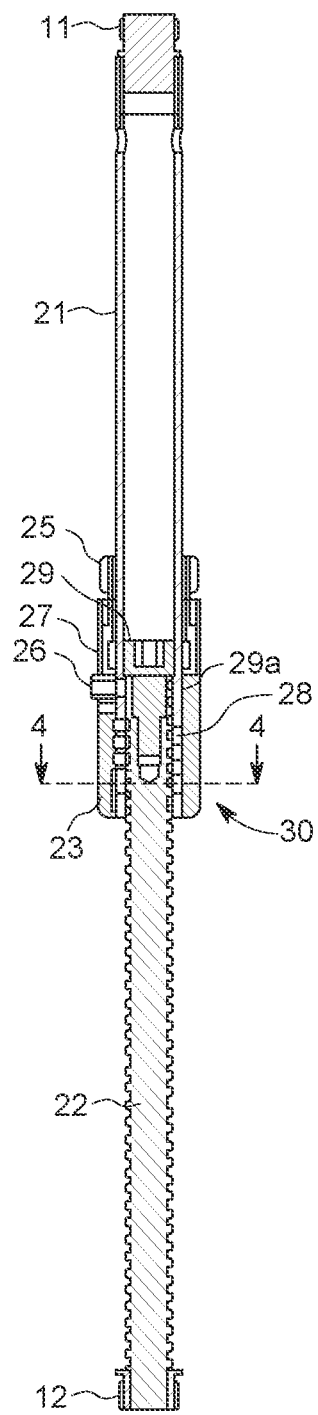
FIG. 3 is a side view in cross-section of the telescopic strut of FIG. 1.

FIG. 3 shows a view in cross-section of the telescopic strut according to FIG. 1. Sleeve 23 can be pushed against action of spring 27 provided on the outer tube 21 and which spring is biased with help of nut 25. Then the sleeve 23 is turned around 90° and is arrested within the other free end of the groove 24. In this embodiment, it is preferred that this position is fixed through nut 25.

The turning angle of 90 degrees is defined in view of the way the quick length adjustment mode is working. This can be seen in FIG. 4 being a representation of a cross section of the rod along line 4-4 in FIG. 3. It can be seen from FIG. 4 that the sleeve 23 has a non-cylindrical inner bore. The bore can be e.g. elliptical. The shorter diameter of the bore is sufficient to accommodate the outer diameter of the foremost portion 25a of outer tube 21, which is cylindrical. Foremost portion 25a comprises on both sides a plurality of preferably, four holes 38 to accommodate one ball 28 each. Of course, it is also possible to provide only two balls on each side or five or more. Three or four balls have been proven to be sufficient without lengthening the sleeve 23 too much.

Figure 4:
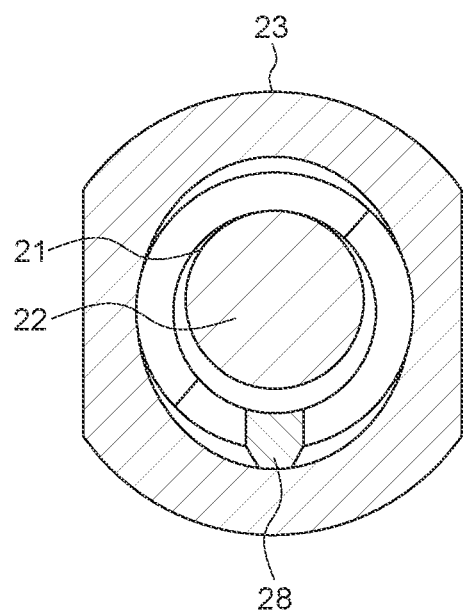
FIG. 4 is a cross-section of the rod along line 4-4 in FIG. 3.

The inner diameter of outer tube 21 is greater than the outer thread portion of the rod 22 which is cylindrical. Therefore, the rod 22 can be pushed into the outer tube 21, when the bolt 26 is in a position which allows the sleeve 32 to be oriented as shown in FIG. 4. Then the balls 28 can freely move against the inner wall of sleeve 23 and the rod 22 can be axially pushed. For that the sum of the outer diameter of the rod 22 and twice the diameter of the balls 28 is less or nearly equal to the inner diameter of the sleeve 23.

It is avoided that the threaded rod 22 can be separated from the outer tube 21 through an abutment screw 29 which is screwed into a corresponding thread within the threaded rod 22 and which can abut on a corresponding shoulder within the tube 21 as shown in FIG. 3.

By turning the sleeve 23 around the bolt 26, i.e. by 90°, the balls 28 will be moved because of the elliptic inner shape within the sleeve 23. In this way the balls 28 are pushed through holes 38 towards the grooves of the thread 22 for interlocking, i.e. connecting the thread with the outer tube 21, because the balls 28 stand within both parts and leave no room to allow a direct axial movement of the threaded rod 22.

In this position the threaded rod 22 still can be moved axially through rotational movement of tube 21 being directly coupled via bolt 26 to sleeve 23 against the threaded rod 22 which can rotate in view of the balls 28 pressed in its threads. This allows the fine adjustment.

Thus the elements allow for a quick change between free axial adjustments of the telescopic strut, if the balls 28 do not engage the threaded rod 22. If the balls do engage rod 22 then a fine adjustment through rotation of the outer tube 21/rod 22 is allowed. The balls 28 are engaging the one or subsequent grooves of the threaded rod 22, e.g. depending on the pitch of the rod. The pitch angle of the thread can be chosen e.g. between 30 and 60 degrees and especially between 40 and 50 degrees.

It is clear that this fine adjustment is only possible, if at least one free end 11 or 12 of the telescopic strut can be rotated while fixed within an external fixator ring.

The prior art quick-release or quick-change mechanism, described in U.S. Pat. No. 8,057,474 incorporated by reference herein, which allows for easily adjusting between fine and gross length adjustments of a telescopic strut, is a suitable design for the intended use. However, one potential disadvantage of the prior art quick-release mechanism described above is that it may be relatively expensive to manufacture. Other attempts have been made to create alternative quick-release mechanisms. For example, U.S. Pat. No. 8,574,232, the disclosure of which is hereby incorporated by reference herein, describes a quick-adjust mechanism that allows for rapid strut length adjustment or gradual strut length adjustment, but the gradual strut length adjustment relies on a compression member to press an outer sleeve against an inner sleeve. Relying on compression to maintain strut components engaged for gradual adjustment may be problematic, as such compression members are apt to fail, particularly when under load. If that compression member fails, the strut may unintentionally switch to a rapid adjustment configuration where the strut is free to change lengths, which could cause injury to a patient. Still further, U.S. Pat. No. 8,864,763, the disclosure of which is incorporated herein by reference, describes a strut with a quick-release mechanism that can transition between a rapid adjustment mode and a gradual adjustment mode by clamping threaded fingers of a collet onto an externally threaded component to provide engagement for gradual adjustment, and a rapid adjustment mode by allowing the collet to disengage the externally threaded component. However, this type of system may have drawbacks as well, and may also be likely to unintentionally transition from the gradual adjustment mode to the rapid adjustment mode when under a load that causes the threads of the collet member to disengage from the externally threaded member. The quick release mechanisms described below achieve a highly stable construct that is unlikely to unintentionally transition from the gradual adjustment mode to the rapid adjustment mode, while also being relatively inexpensive to manufacture compared to prior art systems.

Figure 5:
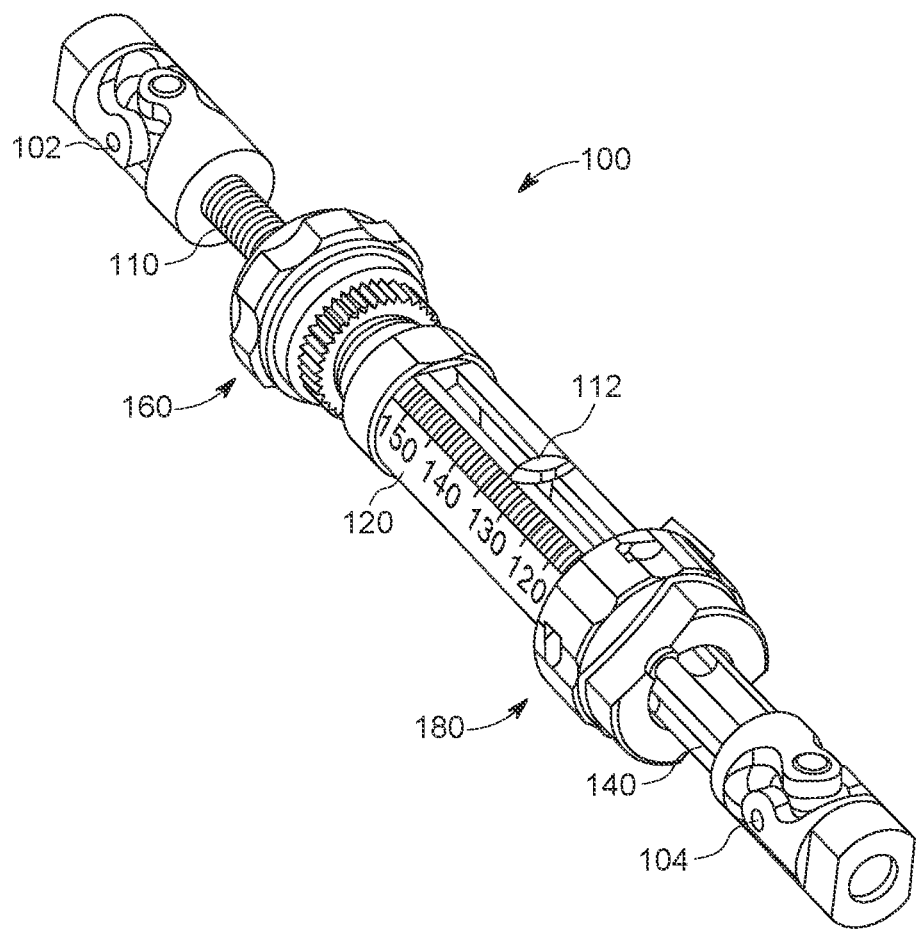
FIG. 5 is a perspective view of a telescoping strut according to an embodiment of the disclosure.

FIG. 5 illustrates a perspective view of a telescopic strut 100 for use with an external fixation system, for example one including two fixation rings intended to be fixed to a bone on opposite sides of a bone deformity. As explained above, an external fixation system will typically include a plurality of the struts 100, such as six struts, that couple the two rings together. Generally, strut 100 may include a joint 102 on one end of the strut 100, and a joint 104 on an opposite end of the strut 100. Joint 102 is illustrated as a universal joint with an opening to allow for a bolt to connect joint 102 to a first fixator ring through a hole of the first fixator ring, and joint 104 is similarly illustrated as a universal joint with an opening (not visible in FIG. 5) to allow for a bolt to connect joint 104 to a second fixator ring through a hole of the second fixator ring. However, it should be understood that the joints 102, 104 may take other forms, including constrained hinge joints, and the joints need not be the same type of joint as each other. Also, the mechanism for attaching the strut 100 to the fixator rings may be other than the bolt connection described above.

Still referring to FIG. 5, strut 100 may additionally include a threaded rod 110, an outer tube 120, an inner tube 140, a fine adjustment knob 160, and a gross adjustment knob 180. Although the term "knob" is used, these components may be generally referred to as actuators, and it should be understood that other designs may be suitable for use as an adjustment mechanism other than a "knob," and the term "knob" includes such alternative designs unless specifically noted otherwise. The strut 100 illustrated in FIG. 5 may be thought of as a "double" telescoping strut, as there are two pairs of components that are capable of telescoping relative to each other. However, the concepts described herein may be generally applicable to "single" telescoping struts, and the invention is not limited to double telescoping struts.

Figure 6A:
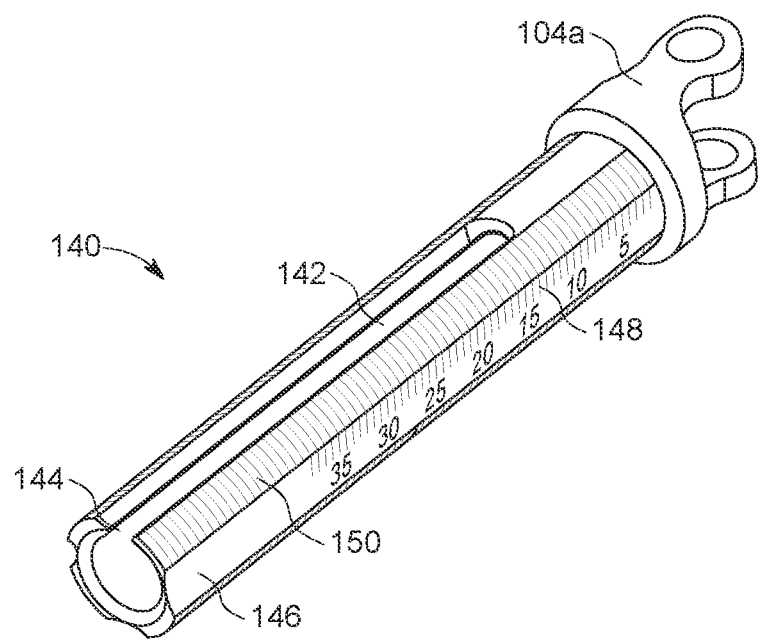
FIGS. 6A-B are perspective views of an inner tube of the strut of FIG. 5.
Figure 6B:
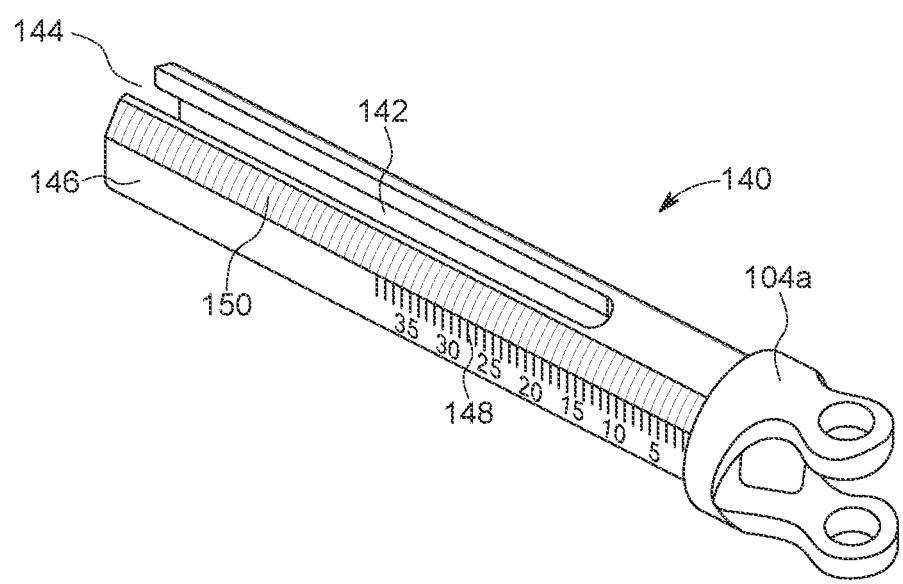

FIGS. 6A-B are perspective views of inner tube 140. In the illustrated embodiment, the inner tube 140 extends from a first end that includes a portion 104a of joint 104, to a second end. It should be understood that joint portion 104a may take other forms than that illustrated, but in the illustrated example, joint portion 140a may be a yolk that includes two extensions with apertures configured to couple to a pin/bearing, which itself may be configured to couple to another yolk to complete the universal joint. The inner tube 140 may be generally hollow, and may be configured to receive threaded rod 110 therein, at least in certain conditions of the strut 100.

Figure 6E:
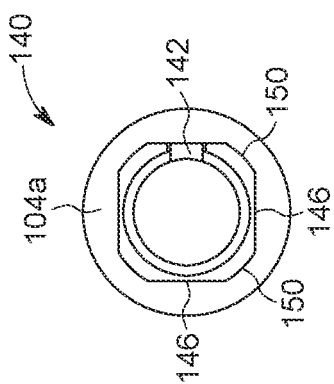
FIG. 6E is a top view of the inner tube of FIGS. 6A-B.
Figure 6D:
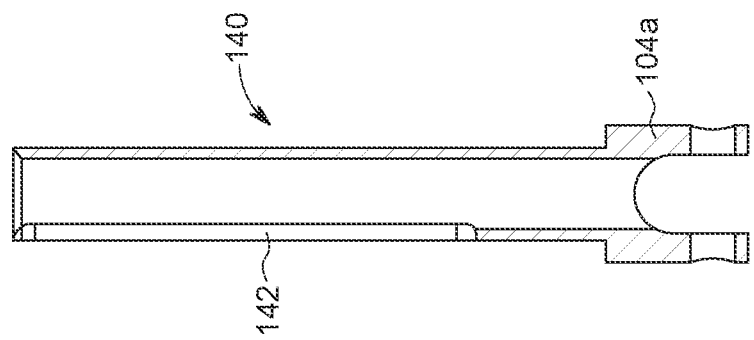
FIG. 6D is a cross-section of the inner tube of FIG. 6C taken along section line 6D-6D of FIG. 6C.
Figure 6C:
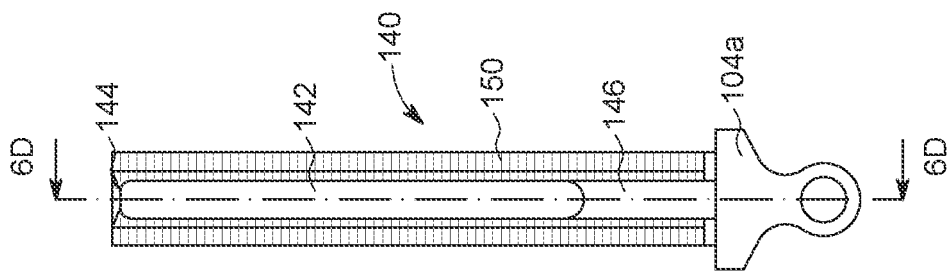
FIG. 6C is a side view of the inner tube of FIGS. 6A-B.

FIG. 6C is a side view of inner tube 140, and FIG. 6D is a cross-section of the inner tube 140 taken along section line 6D-6D of FIG. 6C. Referring to FIGS. 6A-D, inner tube 140 may include a slot 142 that extends to and through one end of the inner tube 140 (the end opposite joint portion 140a), and to a second closed end a spaced distance from joint portion 104a. In other words, a length of inner tube 140 near joint portion 104a is fully circumferentially continuous and uninterrupted by slot 142, with the slot 142 extending the remaining length of the inner tube 140 including at the terminal end of the inner tube 140 opposite the joint portion 104a. As best seen in FIG. 6C, the terminal end of the slot 142 nearer joint portion 104a may be generally rounded, and the terminal end of the slot 142 farthest away from the joint portion 104a may have a slightly narrowed width portion 144. As is described in greater detail below, this narrowed width portion 144 may be sized to allow certain components sliding within slot 142 to pass beyond the narrowed width portion 144, while restricting other components sliding within slot 142 from passing beyond the narrowed width portion 144.

FIG. 6E is a top view of inner tube 140, viewed so that the joint portion 104a is farthest away from the viewer. Referring to FIGS. 6A-C and 6E, the tubular portion of inner tube 140 may have a generally rectangular or square shape, with four flat and/or unthreaded (or un-texturized) surfaces 146 (one of which defines slot 142). At least one of the flat surfaces 146 may include indicia 148 that may be used to help indicate the length of the strut 100. In the illustrated embodiment, indicia 148 take the form of hash marks with numbers printed or otherwise provided thereon—although it should be understood that other types of indicia 148 may be suitable. Each of the four flat surfaces 146 may couple or transition to each other by flat or rounded corners 150. Each of the corners 150 may include texturized surfaces extending part of or the entire length of the inner tube 140, excluding the joint portion 104a. The texturized surfaces may be threads, serrations, ridges, or other similar features intended to engage with corresponding texturized surfaces 182a of the gross adjustment knob 180, as described in greater detail below. It should be understood that, although the term "flat" is used in connection with surfaces 146 and corners 150, these surfaces need not be perfectly flat and may include some level of contouring in the circumferential direction.

Figure 7A:
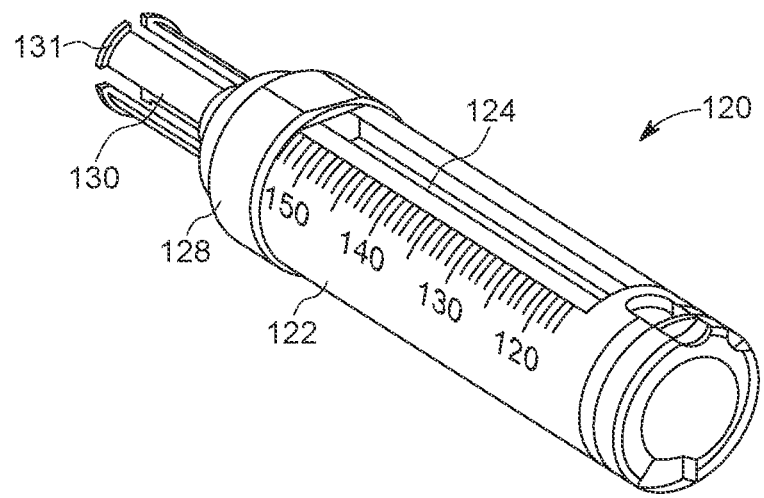
FIG. 7A is a perspective view of an outer tube of the strut of FIG. 5.

FIG. 7A is a perspective view of outer tube 120. In the illustrated embodiment, the outer tube 120 extends from a first end (to the right in the view of FIG. 7A) configured to couple to inner tube 140 via gross adjustment knob 180, to a second end (to the left in the view of FIG. 7A) configured to couple to the threaded rod 110 via fine adjustment knob 160. The outer tube 120 may be generally hollow, and may be configured to receive portions of both the threaded rod 110 and the inner tube 140 therein, at least in certain conditions of the strut 100.

Figure 7B:
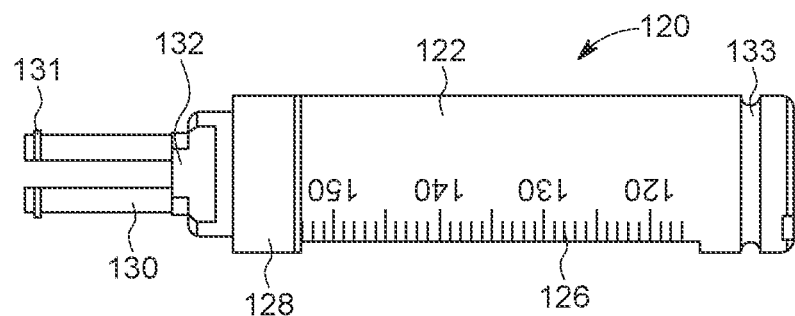
FIGS. 7B-C are side views of the outer tube of FIG. 7A.
Figure 7C:
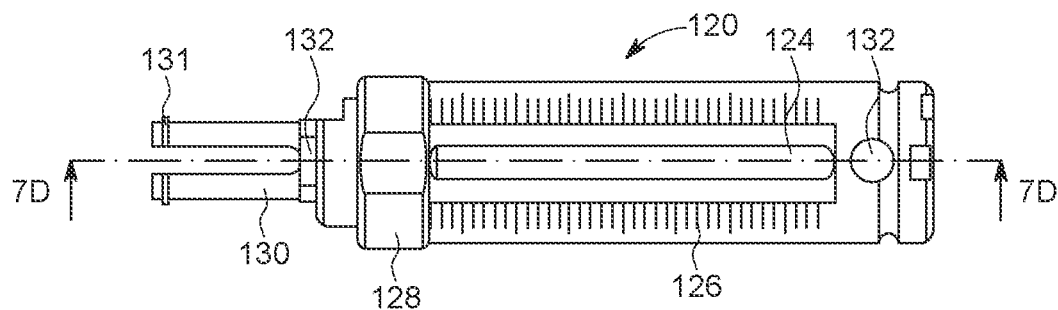
Figure 7D:
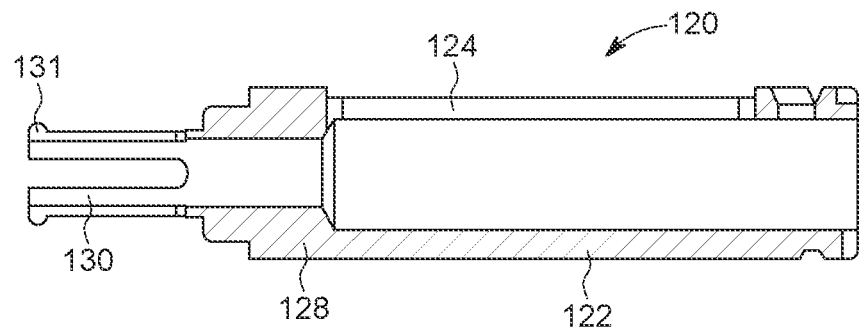
FIG. 7D is a cross-section of the outer tube of FIG. 7C taken along the section line 7D-7D of FIG. 7C.

FIGS. 7B-C are side views of outer tube 120, and FIG. 7D is a cross-section of outer tube 120 taken along section line 7D-7D of FIG. 7C. Referring generally to FIGS. 7A-D, outer tube 120 may include a main body 122 that is generally cylindrical. As best seen in FIGS. 7A, 7C and 7D, the main body 122 may define a slot 124 extending in the longitudinal direction of the main body 122, the slot 124 being closed at each longitudinal end. The portion of main body 122 adjacent the slot 124 may be generally flat, with the remainder of main body 122 being generally cylindrical or circular. As described in greater detail below, the slot 124 may be sized and shaped to receive a portion of a length indicator 112 therethrough. The flat portion of main body 122 may provide a surface against which part of length indicator 112—may slide and/or may help limit the length indicator 112 from protruding beyond the main body, which may help reduce the likelihood the length indicator 112 may get caught on some external structure like a patient's clothes, bed sheets, etc. The main body 122 may include indicia 126, which may be in the form of hash marks and numbers printed or otherwise provided with the hash marks, to help indicate a length of the strut 100 in combination with the length indicator 112. However, as with indicia 148, indicia 126 may take other forms than hash marks with printed numbers.

One end of the main body 122 (to the left in the view of FIG. 7A) may include a collar 128. The collar 128 may be integral with the main body 122, or be formed separately and attached thereto. As best shown in FIGS. 7A and 7C, the collar 128 may be generally cylindrical or circular, with a flat area that aligns with the flat portion of main body 122 adjacent slot 124. A plurality of flexible extensions 130 may extend from the collar 128 in a direction away from the main body 122. In the illustrated embodiment, four flexible extensions 130 are provided. The flexibility of the extension 130 may be achieved, for example, by forming them with relatively thin walls (e.g. compared to the walls of the main body 122) and/or by providing slots between adjacent ones of the extensions 130. In other embodiments, more or fewer than four flexible extensions 130 may be provided. Each extension 130 preferably ends in a protrusion or lip 131 extending radially outward from the center longitudinal axis of the outer tube 120. As is explained in greater detail, the lips 131 may help secure the outer tube 120 to the fine adjustment knob 160.

Figure 7E:
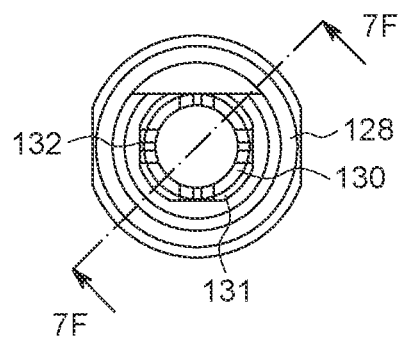
FIG. 7E is a first end view of the outer tube of FIG. 7A.
Figure 7F:
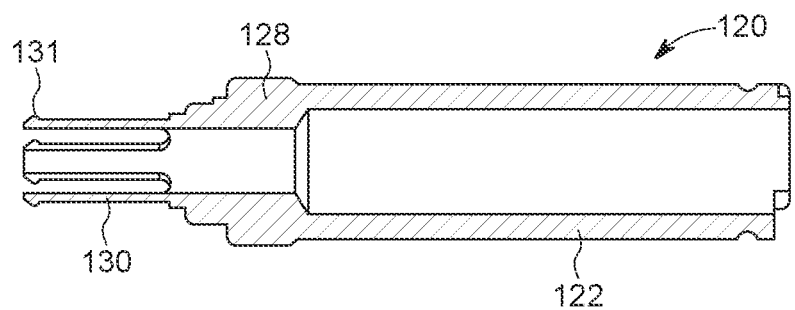
FIG. 7F is a cross-section of the outer tube of FIG. 7E taken along the section line 7F-7F of FIG. 7E.

The extensions 130, in combination, may form a generally cylindrical surface that is interrupted by longitudinal slots between adjacent extensions 130. This is best shown in FIG. 7E, which is an end view of the outer tube 120 with the extensions 130 being closest to the viewer in FIG. 7E. FIG. 7F is a cross-section of outer tube 120 taken along the section line 7F-7F of FIG. 7E. A base area may be positioned between the collar 128 and the beginning of each of the extensions 130. That base may be generally cylindrical or circular, with circumferentially spaced flats 132, best illustrated in FIGS. 7B-C. Each flat 132 may be positioned on the base generally aligned with a slot between circumferentially adjacent extensions 130. As is explained in greater detail below, these flats 132 provide for discrete rotational positions between the outer tube 120 and the fine adjustment knob 160 during gradual adjustment of the length of the strut 100.

Figure 7G:
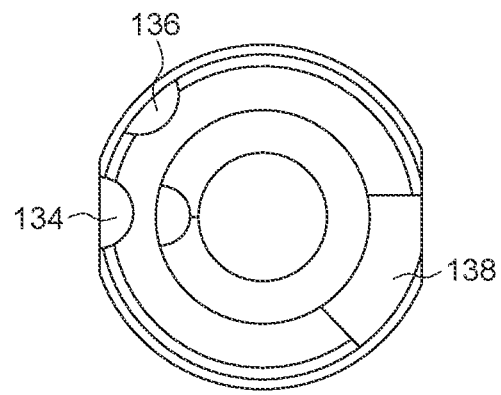
FIG. 7G is a second end view of the outer tube of FIG. 7A.
Figure 7H:
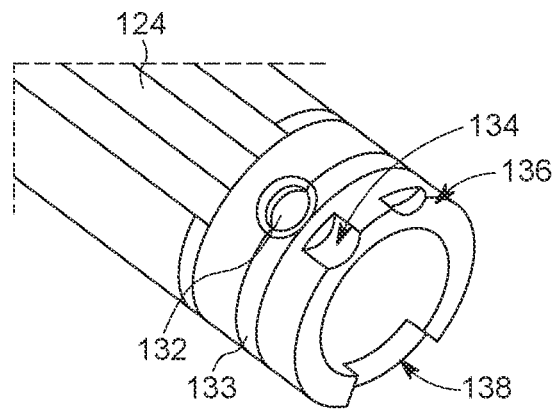
FIG. 7H is an enlarged perspective view of one end of the outer tube of FIG. 7A.

The other end of the main body 122 (to the right in the view of FIG. 7A) may include a number of features for use in engagement with gross adjustment knob 180. FIG. 7G illustrates an end view of outer tube 120, opposite the end shown in FIG. 7E. FIG. 7H is a perspective view of the end of outer tube 120 illustrated in FIG. 7G. Referring mainly to FIGS. 7H, this end of main body 122 may include an aperture 132 extending through the wall of the main body 122, the aperture 132 being longitudinally aligned with slot 124. This aperture 132 may be configured to receive a pin 196 that also passes through slot 142 of inner tube 140, helping to ensure that inner tube 140 and outer tube 120 remain rotationally fixed to one another. Pin 196 may have a width or diameter that is smaller than the width of slot 142, but larger than the narrowed width portion 144 of slot 142, such that the pin 196 also prevents the inner tube 140 from separating or pulling out of the outer tube 120.

This end of the body may also include a circumferential groove or recess 133 that may receive a pin, bearing, o-ring, gasket, or other structure, which is also received within a portion of gross adjustment knob 180, to allow for at least some rotation of gross adjustment knob 180 relative to outer tube 120, while preventing relative axial or translational movement between the gross adjustment knob 180 and outer tube 120. A first detent 134 and a second detent 136 may be provided in the terminal end of outer tube 120, for example at about 45 degrees apart along the circumference of the outer tube 120. As described in greater detail below, detents 134, 136 may act to receive a portion (e.g. a shoulder 186c) of a quick-release pin 186 therein to lock the gross adjustment knob 180 in a locked or unlocked position. A recessed area 138 may be provided in the terminal end of outer tube 120, and recessed area 138 may be generally diametrically opposed to the position of the detents 134, 136. As explained in greater detail below, a rotation limiting pin 194 of the gross adjustment knob 180 may be received within the recessed area 138. The recessed area 138 may extend along about 45 degrees of the circumference of the outer tube 120. As explained in greater detail below, this configuration may allow for the gross adjustment knob 180 to have a total available amount of rotation of about 45 degrees relative to the outer tube 120.

Referring back to FIG. 5, the threaded rod 110 may have a first end fixed to a portion of joint 102 (toward the top of the view of FIG. 5). The majority of threaded rod 110 may be a solid generally cylindrical member with external threading that interacts with corresponding internal threading of fine adjustment knob 160, described in greater detail below. The terminal end of threaded rod 110, opposite the side of joint 102, may exclude threading and have a collar member to which length indicator 112 is coupled. The length indicator 112 is preferably axially fixed with respect to threaded rod 110, but rotationally free. The length indicator 112 may include a relatively narrow portion that is sized and shaped to protrude through both slot 124 in outer tube 120 and slot 142 in inner tube 140. The end of length indicator 112 may be wider than the width of the slot 124, and include extensions that are parallel to the hash marks of indicia 126, to allow a user to readily identify what hash marks or other indicia 126 that the length indicator 112 is pointing. The relatively narrow portion of length indicator 112 may be narrower than the narrowed width portion 144 of slot 142 of inner tube 140, so that the length indicator 112 may pass beyond the end of slot 142 in certain elongated conditions of strut 100. Collar mechanisms to allow for axial fixation but rotational freedom of length indicator 112 are shown in more detail, for example, in U.S. Pat. No. 10,010,350, the disclosure of which is hereby incorporated by reference herein. As should be understood, as the threaded rod 110 rotates and telescopes into or out of the outer tube 120 (and/or into or out of the inner tube 140), the length indicator 112 is capable of sliding along the slots 124, 142 without rotation, even though the threaded rod 110 is rotating.

Figure 8A:
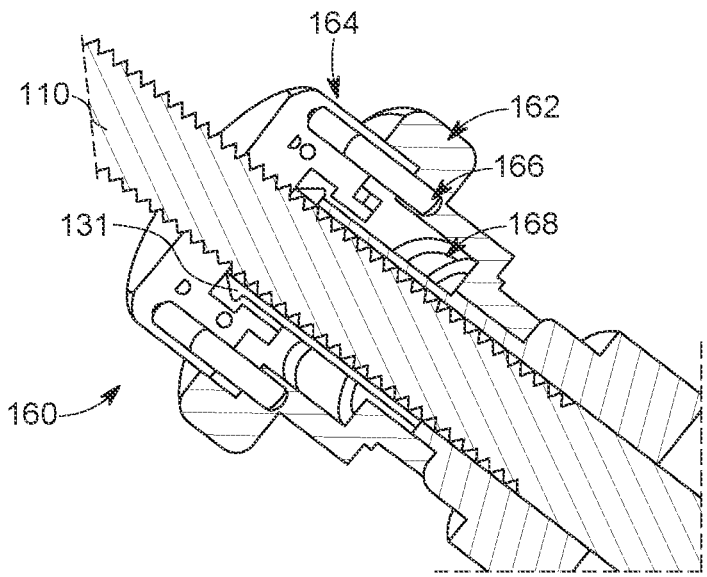
FIGS. 8A-8B are cutaway views of a gradual correction knob of the strut of FIG. 5 in engaged and disengaged conditions, respectively.
Figure 8B:
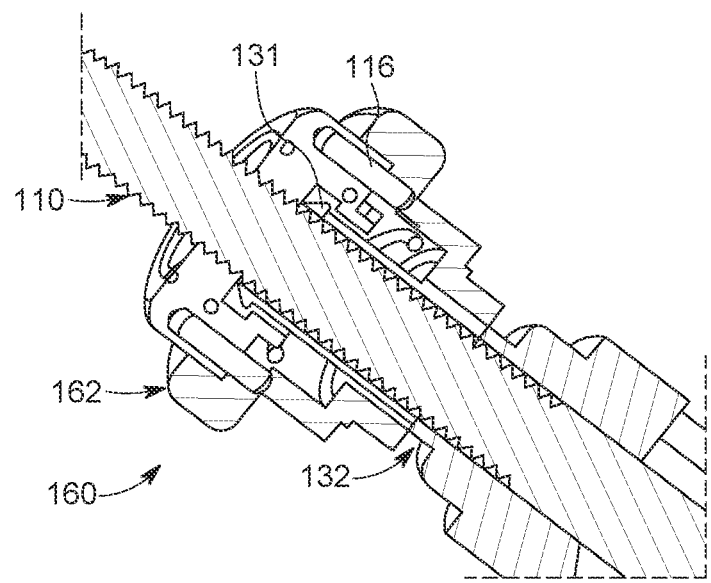

FIGS. 8A-8D illustrated various views of strut 100 in an assembled condition, focusing on the assembly of the gradual connection knob 160 to the threaded rod 110 and outer tube 120. In particular, FIG. 8A shows a cross-section of the gradual correction knob 160 in an engaged or locked state, and FIG. 8B shows the same cross-section in a disengaged or unlocked state. Generally, gradual correction knob 160 may include a thumb knob 162 and a correction wheel 164, although the terms "knob" and "wheel" do not necessarily require any specific structure related to a knob or a wheel.

The correction wheel 164 may include an aperture, for example along a central longitudinal axis, defined by an internally threaded structure of the correction wheel 164. The internal threads may be complementary to and engage the external threads of the threaded rod 110 that extends therethrough, so that the correction wheel 164 is only able to translate relative to threaded rod 110 via relative rotation between the threaded rod 110 and the correction wheel 164. The correction wheel 164 may be coupled to the thumb knob 162 by a plurality of pins 166 (e.g. two, three, four etc.). In the illustrated embodiment, the correction wheel 164 and thumb knob 162 each include channels therein that align with one another (e.g. four channels spaced circumferentially), the channels each configured to receive at least a portion of the pins 166 so that rotation of the thumb knob 162 causes rotation of the correction wheel 164. In the illustrated embodiment, the thumb knob 162 may include bumps, ridges, or other textures to provide easier gripping of the thumb knob 162.

The correction wheel 164 may include an internal recessed shoulder sized and shaped to receive the protrusions or lips 131 of the flexible extensions 130 of the outer tube 120. One end of the thumb knob 162 may have an opening sized and shaped to receive the flexible extensions 130 of the outer tube 120 therethrough. With this configuration, when assembled, the flexible extensions pas through the center of the thumb knob 162 and into an interior area of the correction wheel 164, with the protrusions or lips 131 of the flexible extensions 130 extending into the complementary recessed shoulder of the correction wheel 164. This configuration helps ensure that, as the correction wheel 164 rotates relative to (and thus translates relative to) the threaded rod 110, the outer tube 120 is pulled or pushed along with the gradual correction knob 160 as it translates along the threaded rod 110. It should be understood that the external threads of the threaded rod 110 do not intermesh with any internal threading of the outer tube 120, allowing for the outer tube 120 to translate along the threaded rod 110 without the outer tube 120 rotating.

The distal end of the thumb knob 162 may include flat areas positioned in a complementary way to the flats 132 adjacent the collar 128 of the outer tube 120. For example, if the outer tube 120 includes four flats 132 arranged in a square pattern, the distal end of the thumb knob 162 may include a corresponding four flats in a square pattern. However, it should be understood that different numbers of corresponding flats may instead be provided. With this configuration, when the gradual correction knob 160 is in the locked or engaged condition shown in FIG. 8A, the flats 132 of the outer tube 120 engage the corresponding flats of the thumb knob 162, restricting the ability of the thumb knob 162 (and thus the correction wheel 164) from rotating relative to the outer tube 120. This locked or engaged position may be the default position. This default position may be maintained by a biasing element, for example spring 168, which may have a first end pressing against the thumb wheel 162 and a second end pressing against the correction wheel 164. In order to transition the gradual correction knob 160 to the disengaged or unlocked condition, a user may pull the thumb wheel 162 proximally toward the correction wheel 164 to compress the spring 168. With the spring 168 compressed, as shown in FIG. 8B, the flats of the distal end of the thumb wheel 162 clear the corresponding flats 132 on the outer tube 120, freeing the thumb wheel 162 (and thus the correction wheel 164) for rotation relative to the outer tube 120 and relative to the threaded rod 110. As the thumb wheel 162 is rotated, the pins 116 transfer force to the correction wheel 164 to cause the correction wheel 164 to rotate, resulting in translation of the gradual correction knob 160 (and thus the outer tube 120) up or down the threaded rod 110. As rotation continues, the flats 132 of the outer tube 120 will again soon align with corresponding flats of the distal end of the thumb wheel 162, with the force of spring 168 pressing the thumb wheel 162 back into engagement with the flats, automatically returning the gradual correction knob 160 to the locked or engaged condition shown in FIG. 8A. This allows for discrete, gradual, and incremental adjustment of the length of strut 100 via discrete "clicks," with each "click" representing a quarter turn of the gradual correction knob 160. However, it should be understood that if more flats, e.g. eight flats in an octagon pattern, are provided, each "click" would represent a smaller increment of a full turn, and vice versa.

Although not shown in FIGS. 8A-B, an additional gear mechanism 170 may be provided below the thumb wheel 162, as shown in FIGS. 8C-8D. This gear 170 may be adapted to engage a complementary gear of a motorized adjustment module (not shown) that may be snapped onto the strut. When the motorized adjustment module is snapped onto the strut, a collar may be positioned between the proximal end of the gear 170 and the distal end of the thumb knob 162, causing the spring 168 to remain compressed while the motorized adjustment module is coupled to the strut 100. This allows for infinitesimally small length adjustment by rotating gear 170 via the complementary gear of the motorized adjustment module as long as the motorized adjustment module is coupled to the strut.

FIGS. 9A-H are various views of gross adjustment knob 180 that may, along with other components, function as a "quick-release" or "quick-change" mechanism to allow for rapid adjustment of the length of strut 100, typically during coupling of the struts 100 to the rings of the external fixation frame. The use of this quick-release mechanism is described in greater detail below following the description of the structure of the components that form, at least in part, this quick-release mechanism.

Figure 9A:
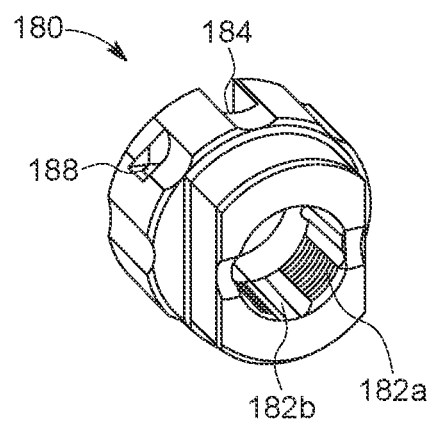
FIG. 9A is a perspective view of a gross adjustment knob of the strut of FIG. 5.
Figure 9B:
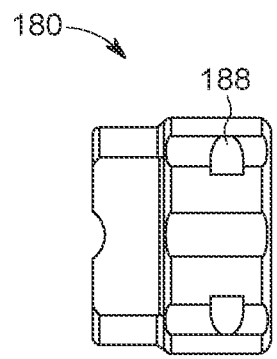
FIG. 9B is a side view of the gross adjustment knob of FIG. 9A.
Figure 9C:
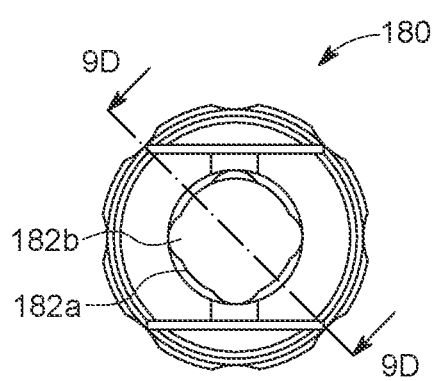
FIG. 9C is a top view of the gross adjustment knob of FIG. 9A.
Figure 9D:
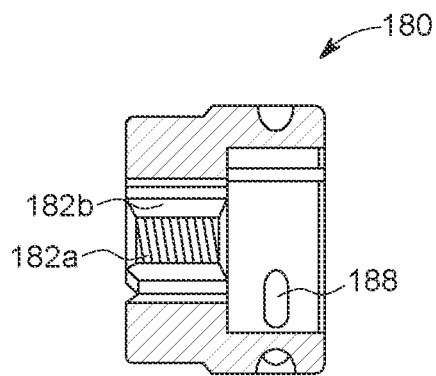
FIG. 9D is a section of the gross adjustment knob of FIG. 9C taken along section line 9D-9D of FIG. 9C.
Figure 9E:
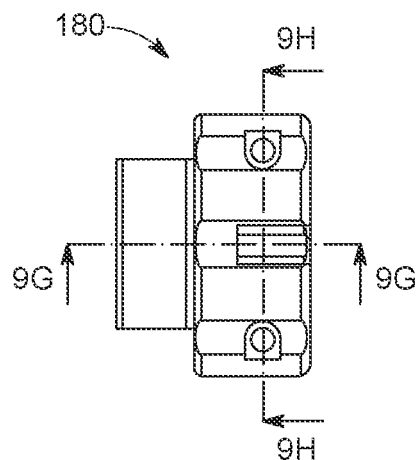
FIG. 9E is another side view of the gross adjustment knob of FIG. 9A.
Figure 9F:
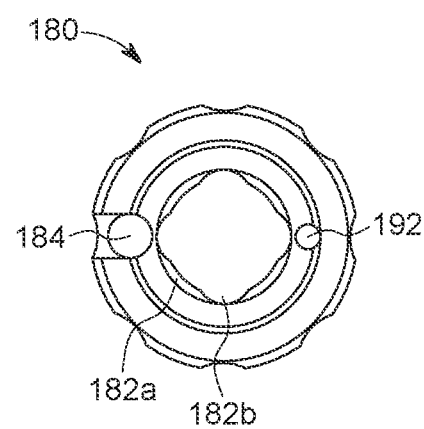
FIG. 9F is a bottom view of the gross adjustment knob of FIG. 9A.

The gross adjustment knob 180 may include bumps, ridges, or other textures to provide easier gripping of the gross adjustment knob 180. The gross adjustment knob 180 may define an aperture extending therethrough, the aperture defining a channel that is generally cylindrical, with certain exceptions noted below. The gross adjustment knob 180 may define a plurality of threaded areas 182a extending along part of the length of the channel. In the illustrated embodiment, there are four threaded areas 182a, each threaded area 182a being circumferentially spaced from an adjacent threaded area 182a by a non-threaded area 182b. Although four threaded areas 182a and four non-threaded areas 182b are illustrated, it should be understood that more or fewer threaded areas 182a and non-threaded areas 182b may be provided, primarily depending on the number of threaded corners 150 provided on the inner tube 140. In other words, the number of threaded corners 150, threaded areas 182a, and non-threaded areas 182b are preferably equal, whether four of each are provided as in in the illustrated embodiment, or if more or fewer are provided. Further, as with threaded corners 150, although the term threaded area 182 is used, the area may include texturizations other than threads, such as serrations, ridges, etc., as long as the texturization is configured for robust engagement with the corresponding texturizations on threaded corners 150. The engagement of inner tube 140 with gross adjustment knob 180 is described in more detail below after the structural description of gross adjustment knob 180. As best seen in FIGS. 9C and 9F, the texturization of threaded areas 182a extends radially inward toward a center of the channel of the gross adjustment knob 180, so that a circle traced along the threaded areas 182a has a smaller diameter than a circle traced along the non-threaded areas 182b. As is described in great detail below, this allows for selective engagement between the threaded areas 182 and the threaded corners 150 of inner tube 140.

Figure 9G:
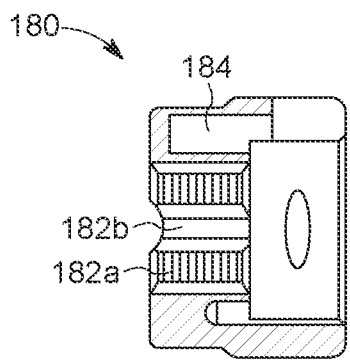
FIG. 9G is a cross-section of the gross adjustment knob of FIG. 9E taken along the section line 9G-9G of FIG. 9E.
Figure 9H:
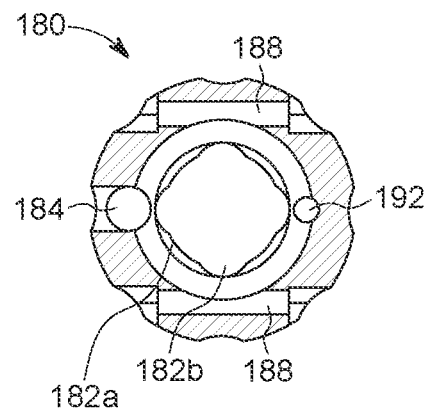
FIG. 9H is a cross-section of the gross adjustment knob of FIG. 9E taken along the section line 9H-9H of FIG. 9E.
Figure 10A:
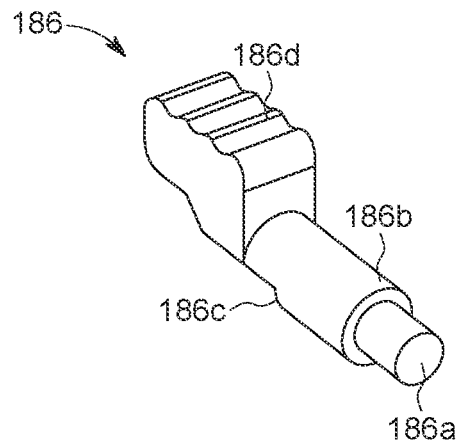
FIGS. 10A-B are perspective and side views, respectively, of a quick-release pin of the strut of FIG. 5.
Figure 10B:
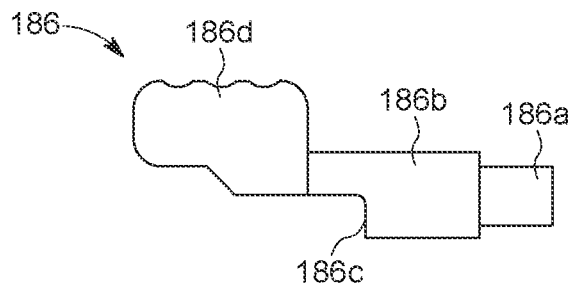

As best seen in FIGS. 9F-H, the gross adjustment knob 180 may include a quick-release pin channel 184 extending partially therethrough, in a direction generally parallel the central longitudinal axis. One end of the quick-release pin channel 184 may be closed, and the opposite end may be open. As described in greater detail below, the quick-release pin channel 184 may be sized and shaped to receive a spring (or other biasing member) 185 therein, and to also receive a quick-release pin 186 at least partially therein. The quick-release pin 186 is illustrated in FIGS. 10A-B. Briefly, quick-release pin 186 may include a generally cylindrical protrusion 186a sized to pass into the center of a spring 185 (illustrated in FIGS. 11E-F) so that a face of spring is in contact with a larger generally cylindrical body 186b of the quick-release pin 186. As described in further detail below, the quick-release pin 186 may also include a shoulder 186c, and a textured or grip portion 186d which the user may handle.

Referring again to FIGS. 9A-H, the gross adjustment knob 180 may include two pin channels 188 extending in a direction transverse or orthogonal to the central channel, with each pin channel 188 being generally parallel to each other and positioned on opposite sides of the central channel. These pin channels 188, best shown in FIG. 9H, may be located in the portion of the gross adjustment knob 180 with the ridges, and may each be sized and shaped to receive a translation limiting pin 190 (illustrated in FIGS. 11C, 11G, 11I), so that the translation limiting pins 190 are positioned at least partly within groove or recess 133 of the outer tube 120 to allow for at least some rotation of the gross adjustment knob 180 with respect to the outer tube 120, while limiting any axial translation of the gross adjustment knob 180 with respect to the outer tube 120. Gross adjustment knob 180 may also include an additional pin channel 192 extending partially therethrough, generally parallel to quick-release pin channel 184 but on an opposite side of the central passageway. As described in greater detail below (illustrated in FIGS. 11E-F), the additional pin channel 192 may be sized and shaped to receive a rotation limiting pin 194 so that a portion of the rotation limiting pin 194 protrudes beyond the additional pin channel 192 and into the recessed area 138 of the outer tube 120.

Figure 11C:
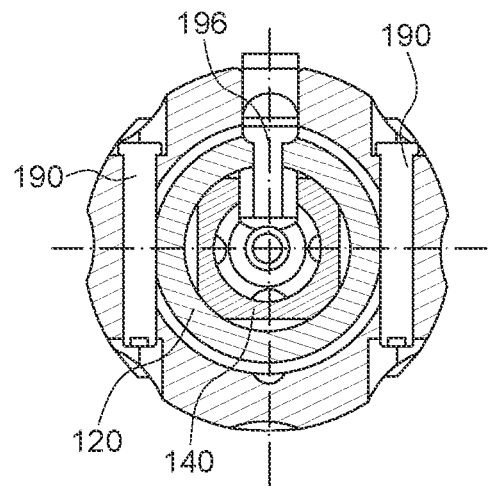
FIG. 11C is a cross-section of the strut of FIG. 11A taken along section line 11C-11C of FIG. 11A.
Figure 11D:
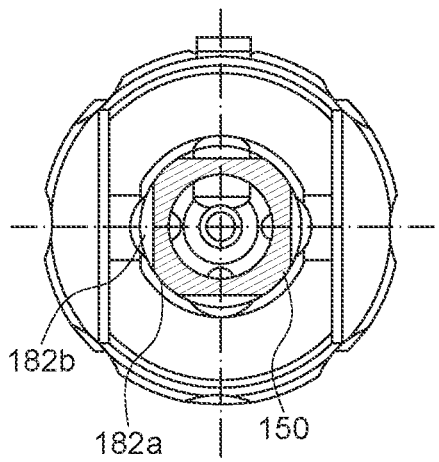
FIG. 11D is a cross-section of the strut of FIG. 11A taken along section line 11D-11D of FIG. 11A.
Figure 11E:
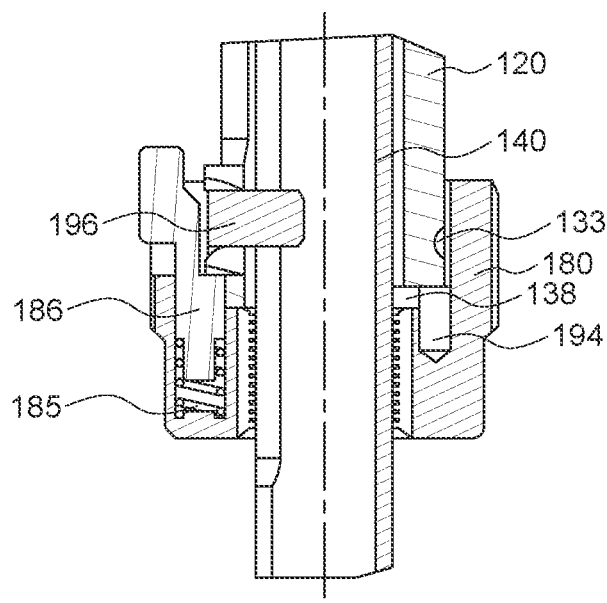
FIG. 11E is an enlarged view of portion 11E of the strut of FIG. 11B.

FIGS. 11A-K illustrate various views of strut 100 to better illustrate the components involved with gross adjustment knob 180. For example, FIG. 11A is a side view of strut 100, and FIG. 11B is a cross-section taken along the section line 11B-11B of FIG. 11A. FIGS. 11C-11E provide additional views focused on the section of the strut 100 in which gross adjustment knob 180 is located. As shown in these figures, when the strut 100 is fully assembled, pin 196 passes through aperture 132 of outer tube 120 and through the slot 142 of inner tube 140, helping to ensure that the outer tube 120 and inner tube 140 remain rotationally fixed to one another during relative translation. Further, as noted above, the pin 196 is sized so that it cannot pass through the terminal end of the slot 142 of inner tube 140 at the narrowed width portion 144, helping to ensure that the inner tube 140 cannot disconnect from the outer tube 120 during relative translation. Pin 196 may be positioned radially inward of the quick-release pin 186, so that the movement of quick-release pin 186 is not inhibited by pin 196.

Figure 11F:
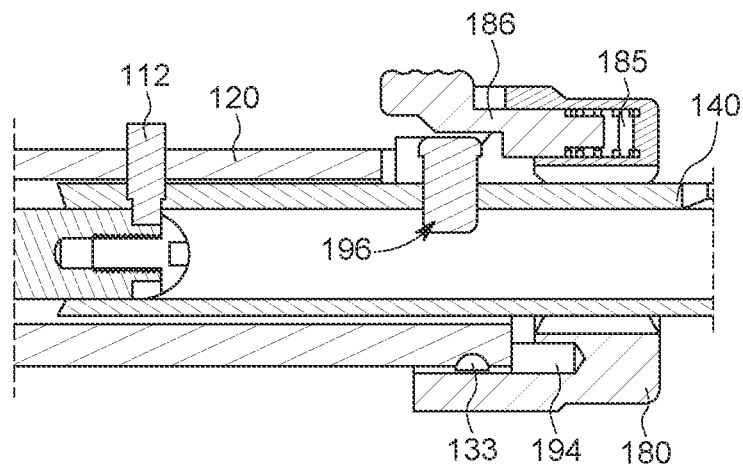
FIGS. 11F-H are cross-sections of the strut of FIG. 11A taken near the gross adjustment knob of the strut.
Figure 11G:
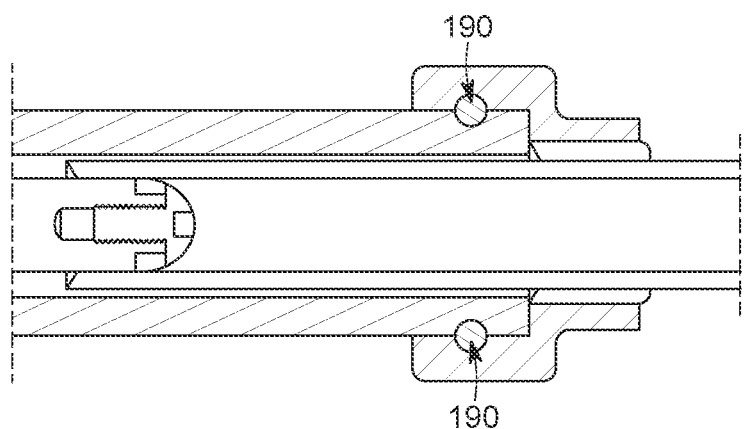
Figure 11H:
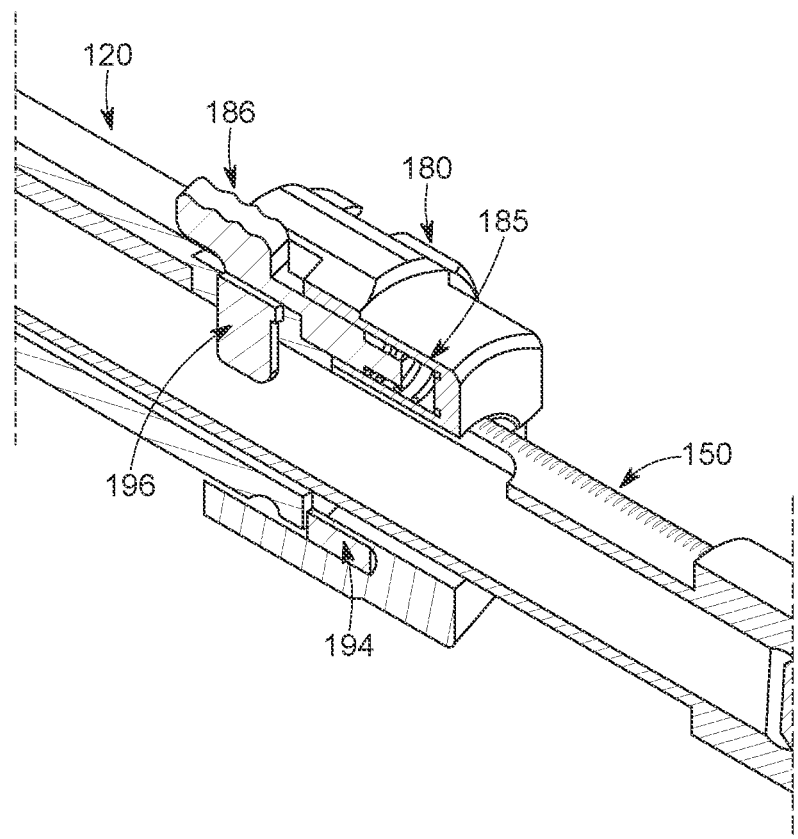
Figure 11I:
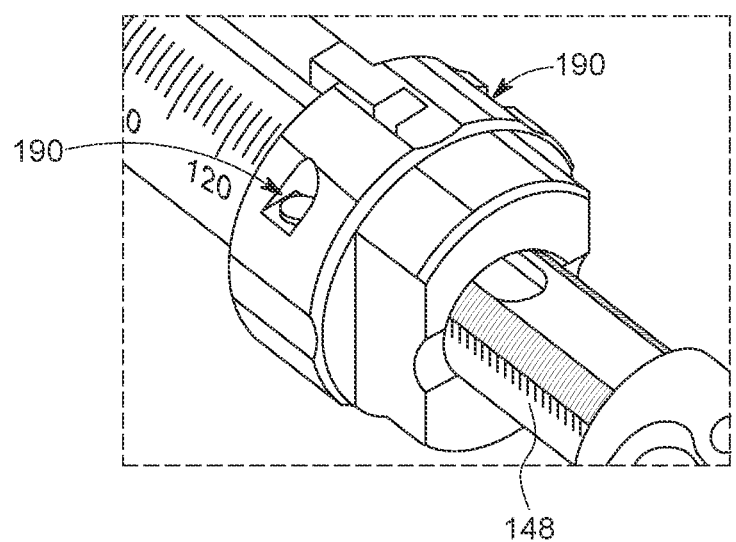
FIG. 11I is an enlarged perspective view of the gross adjustment knob of the strut of FIG. 5.

As best shown in FIGS. 11C, 11G, and 11I, the two translation limiting pins 190 extend through the corresponding pin channels 188 of gross adjustment knob 180 an partially within portions of the recess or groove 133 of the outer tube 120 so that the gross adjustment knob 180 is translationally fixed to, and partly overlies, the terminal end of outer tube 120. As described above, these translation limiting pins 190 themselves do not inhibit rotation of the gross adjustment knob 180 relative to the outer tube 120.

As best shown in FIGS. 11E, 11F, and 11H, rotation limiting pin 194 is received within the additional pin channel 192 of gross adjustment knob 180. A portion of the rotation limiting pin 194 protrudes up beyond the end of the additional pin channel 192, and into the recessed area 138. As the gross adjustment knob 180 rotates relative to the outer tube 120, the rotation limiting pin 194 will eventually contact one or the other end of the recessed area 138, limiting further rotation. In the illustrated strut 100, the rotation limiting pin 194 has a maximum travel of about 45 degrees (or one eighth of a full rotation), although as noted above, in other embodiments the rotation limit could be greater or smaller.

As best shown in FIGS. 11E, 11F, and 11H, spring 185 (or another biasing member) and quick-release pin 186 are both received within the quick-release pin channel 184 of the gross adjustment knob 180. In particular, a first end of the spring 185 may abut the closed end of the quick-release pin channel, with protrusion 186a extending into the center of the spring 185 so that the second end of the spring 185 abuts the larger cylindrical body 186b. The shoulder 186c of the quick-release pin 186 is positioned to abut the terminal end of the outer tube 120. However, the quick-release pin 186 is positioned so that the shoulder 186c can only be positioned adjacent first detent 134, second detent 136, or positions between the two detents. This is a result, at least in part, of the fact that, when the rotation limiting pin 194 is in contact with one end of the recessed area 138, the shoulder 186c is aligned with the first detent 134, and when the rotation limiting pin 194 is in contact with the opposite end of the recessed area 138, the shoulder 186c is aligned with the second detent 136. When the shoulder 186c is aligned with the first detent 134, the spring 185 presses the shoulder 186c into the first detent 134, limiting any further rotation. In order to rotate the gross adjustment knob 180, the spring 185 must be depressed (e.g. by pressing the grip portion 186d of quick-release pin 186) so that the shoulder 186c moves beyond the first detent 134. While the spring 185 is depressed, the gross adjustment knob 180 may be rotated, and rotation may continue until the shoulder 186c aligns with the second detent 136, at which point the spring 185 pushes the shoulder 186c into the second detent 136 to limit further rotation, again until the spring 185 is later depressed.

With the configuration described above, the gross adjustment knob 180 is translationally fixed to the outer tube 120, and is capable of 45 degrees of rotation relative to the outer tube 120, with the gross adjustment knob 180 locking against further rotation when at the maximum amount of rotation in either direction. The gross adjustment knob 180 may be unlocked by depressing the quick-release pin 186, and then manually rotating the gross adjustment knob 180 while the spring 185 is depressed. In other words, this configuration allows for two discrete stable rotational positions of the gross adjustment knob 180 relative to the outer tube 120, with each of these positions automatically locking to prevent any further unintentional rotation.

Figure 11J:
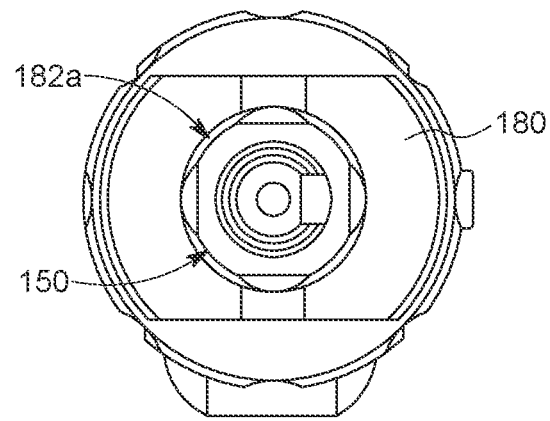
FIGS. 11J-K are end views of the gross adjustment knob of the strut of FIG. 5 in an engaged and disengaged condition, respectively.
Figure 11K:
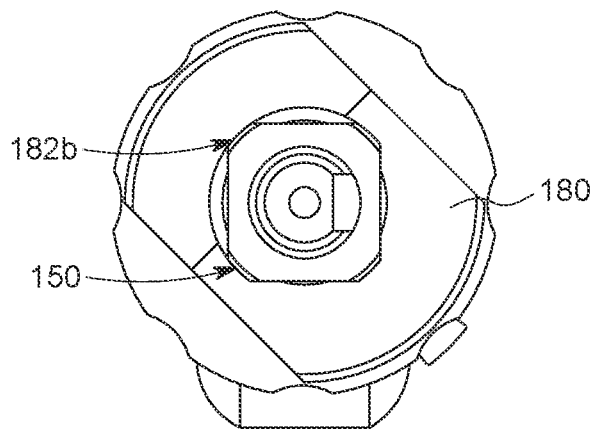

As best shown in FIGS. 11H-K, the inner tube 140 extends through the interior of the gross adjustment knob 180 and into the interior of the outer tube 120, with the inner tube 140 and outer tube 120 being coupled by the pin 196. The inner tube 140 is positioned relative to the gross adjustment knob 180 so that, when the gross adjustment knob 180 is at maximum rotation relative to the outer tube 120 in one direction, the threaded corners 150 of the inner tube 140 engage corresponding threaded areas 182a of the gross adjustment knob 180. However, when the gross adjustment knob 180 is at the maximum rotation to the outer tube 120 in the opposite direction, the threaded corners 150 of the inner tube 140 align with the non-threaded areas 182b of the gross adjustment knob 180. In other words, as shown in FIG. 11J, in one discrete rotational position, the threaded areas 182a of the gross adjustment knob 180 engage with or mesh with the threaded corners 150 of the inner tube 140, so that the inner tube 140 is not capable of axial movement relative to the gross adjustment knob 180. In order to allow for a rapid length adjustment of the strut 100, the quick-release pin 186 may then be depressed, and the gross adjustment knob 180 may be rotated (for example 45 degrees, which may be the maximum rotation allowed by rotation limiting pin 194), until the threaded corners 150 of the inner tube 140 align with the non-threaded areas 182b of the gross adjustment knob 180, as shown in FIG. 11K. In this unlocked condition shown in FIG. 11K, the threaded corners 150 of the inner tube 140 do not engage or mesh with any corresponding threads of the gross adjustment knob 180, and the threaded areas 182a of the gross adjustment knob do not engage or mesh with any corresponding threads of the inner tube 140. In other words, in the unlocked condition shown in FIG. 11K, the inner tube 140 is generally free to translate into or out of the gross adjustment knob 180.

In a typical use of a plurality of struts 100 with an external fixation system that includes two fixator rings, the external fixation system has a desired initial position on the patient that may be determined before or during the surgery. In order to achieve the desired initial position, each strut 100 may have a desired initial length. When assembling the struts 100 to the fixator rings, each strut 100 may be set to the unlocked condition shown in FIG. 11K to allow for rapid length adjustment of the strut 100. Each strut may be rapidly adjusted to the initial desired length, which may be confirmed, at least in part, by comparing the position of the gross adjustment knob 180 to the indicia 148 on the inner tube 140, as best shown in FIG. 11I. When the initial desired length is achieved, the gross adjustment knob 180 may be rotated (after depressing the quick-release pin 186) until the gross adjustment knob 180 transitions to the locked condition, as shown in FIG. 11J. Preferably, although it is not required, the threaded rod 110 is at (or near) a maximum or minimum position relative to the outer tube 120 at this initial phase, which may allow for maximum length adjustment during the correction phase. After each strut 100 is set to its desired initial length, switched to the locked position, and attached to the fixator rings, the correction phase may begin in which the length of each strut 100 is gradually adjusted to correct the bone deformity. As described above, the fine adjustment knob 160 may be actuated in order to drive the threaded rod 110 into or out of the outer tube 120 to decrease or increase the length of the strut 100, respectively. It should be understood that the fine adjustment should typically only be performed when the gross adjustment knob 180 is in the locked condition, in order to ensure the struts 100 only change length the precise desired amount. During correction of the bone deformity, it would be undesirable for the struts 100 to unintentionally switch to the unlocked or "quick-adjust" mode, as the external fixation system may partially or entirely lose stability while connected to the patient's bone. The meshing or engagement between the threaded corners 150 of the inner tube 140 and the threaded areas 182*a* of the gross adjustment knob 180 provide for a very robust connection between the gross adjustment knob 180 and the inner tube 140, ensuring that the gross adjustment knob 180 will remain in the locked condition unless and until the gross adjustment knob 180 is intentionally actuated to transition to the unlocked condition.

Compared to prior art systems, the quick-release mechanism described herein may provide various benefits. First, as noted above, some prior art systems rely on compression to maintain the strut in the locked or engaged condition for gradual or fine adjustment, but such compression mechanisms are prone to failure. On the other hand, the thread-to-thread (or serration-to-serration, etc.) type of engagement in strut 100 to maintain the strut 100 in the locked or engaged condition for fine or gradual length adjustment is significantly more robust and less prone to failure compared to prior art mechanisms. For example, although U.S. Pat. No. 8,864,763 discloses a collet with flexible fingers with threads that engage threads of another member to maintain a device in a locked condition, the device in the '763 patent still relies on compression via a clamp to maintain the locked engagement. The mechanisms described above do not similarly rely on compression. Further, the configurations described herein may be relatively simple and inexpensive to produce compared to other robust locking mechanisms of the prior art, such as that shown in FIG. 2.

Figure 12:
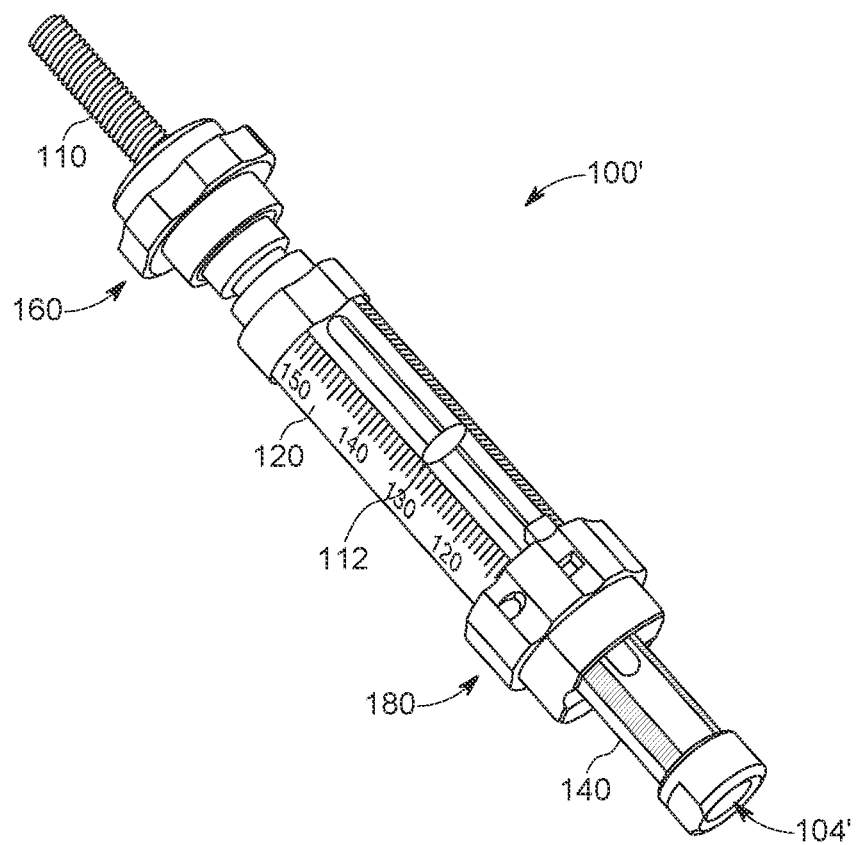
FIG. 12 is a perspective view of a strut, generally similar to that shown in FIG. 5, according to another aspect of the disclosure.

The features described above in connection with the quick-release mechanism may be used, with or without modification, in other struts besides double-telescoping struts with universal joints. For example, FIG. 12 illustrates a strut 100' that is identical in most respects to strut 100, with the exception of joints 102, 104. In a bone transport frame, similar to that shown in U.S. Pat. No. 9,101,398, the disclosure of which is hereby incorporated by reference herein, the struts may lack jointed connections to the proximal and distal rings, and may each be generally parallel to each other during use. Strut 100' may be suitable for use in a bone transport frame, with the joints being removed. Instead, for example, the distal end of strut 100' may include a connector portion 104' with female threads to accept a bolt that passes through a distal-most ring of the bone transport frame. The fine and gross adjustments of strut 100' function identically to those described above in connection with strut 100.

FIGS. 13A-D are various views of another embodiment of gross adjustment knob 180' that is similar to gross adjustment knob 180 in most respects. Thus, for brevity, only the feature of gross adjustment knob 180' that are different from gross adjustment knob 180 are described below. It should be understood that other features and uses of gross adjustment knob 180' may be similar or identical to the corresponding features of gross adjustment knob 180 described above.

The gross adjustment knob 180' may include bumps, ridges, or other textures to provide easier gripping of the gross adjustment knob 180', and may define an aperture extending therethrough, the aperture defining a channel that is generally cylindrical. The gross adjustment knob 180' may define a plurality of threaded areas 182*a*' extending along part of the length of the channel. In the illustrated embodiment, there are four threaded areas 182*a*', each threaded area 182*a*' being circumferentially spaced from an adjacent threaded area 182*a*' by a non-threaded area 182*b*'. Although four threaded areas 182*a*' and four non-threaded areas 182*b*' are illustrated, it should be understood that more or fewer threaded areas 182*a*' and non-threaded areas 182*b*' may be provided, primarily depending on the number of threaded corners 150 provided on the inner tube 140. As with gross adjustment knob 180, gross adjustment knob 180' may include a quick-release pin channel (not visible in FIGS. 13A-D) sized and shaped to receive a spring (or other biasing member) therein, and to also receive a quick-release pin 186 at least partially therein. Also, as with gross adjustment knob 180, gross adjustment knob 180' may include two pin channels 188' (one of which is visible in FIG. 13A) sized and shaped to receive translation limiting pin 190, and an additional pin channel (not visible in FIGS. 13A-D) sized and shaped to receive rotation limiting pin 194.

As described above in connection with FIGS. 11J-K, in order to transition gross adjustment knob 180 to the locked condition, the gross adjustment knob 180 may be rotated until threads 151 of the threaded corners 150 of the inner tube 140 align with and engage the threaded areas 182*a* of the gross adjustment knob 180, as shown in FIG. 11J. However, when transitioning from the unlocked condition of FIG. 11K to the locked condition of FIG. 11J, there is a possibility that the edges of one or more of the threads of threaded areas 182*a* may contact the edges of one or more of the threads 151 of threaded corners 150, instead of the threads of threaded areas 182*a* aligning between adjacent threads 151 of threaded corners 150. In other words, due to tolerances in manufacturing of the threads of threaded areas 182*a* and threaded corners 150, the threads may not always perfectly mesh with one another when transitioning to the locked condition of FIG. 11J, resulting in "sticking" of the locking mechanism. Such "sticking" may make it difficult or impossible to fully transition the gross adjustment knob 180 to the locked condition. This problem may be solved, or at least mitigated, by introducing one or more scallops, leading edges, or guide threads 187*b*' onto one or more threads 187*a*' of threaded areas 182*a*'. It should be understood that the terms scallops, leading edges, and guide threads are intended to be used interchangeably.

Figure 13A:
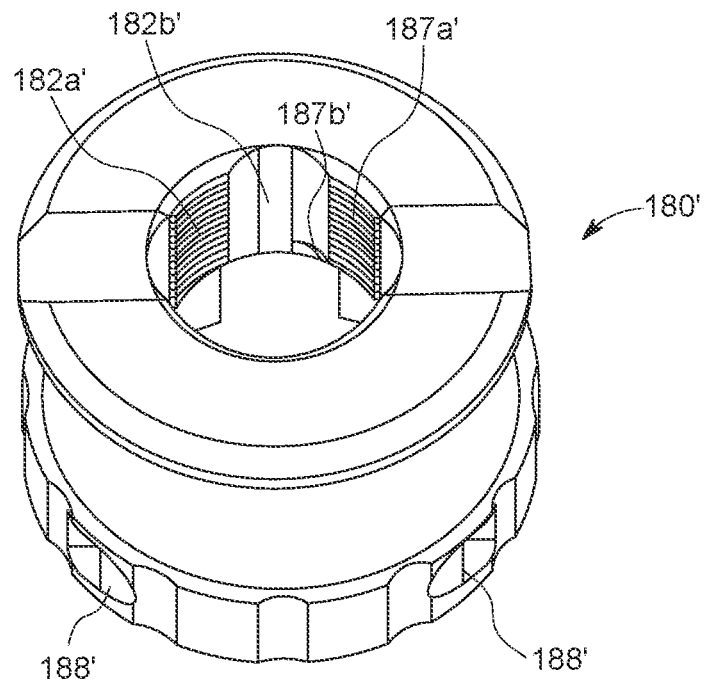
FIG. 13A is a perspective view of a gross adjustment knob according to another embodiment of the disclosure.
Figure 13B:
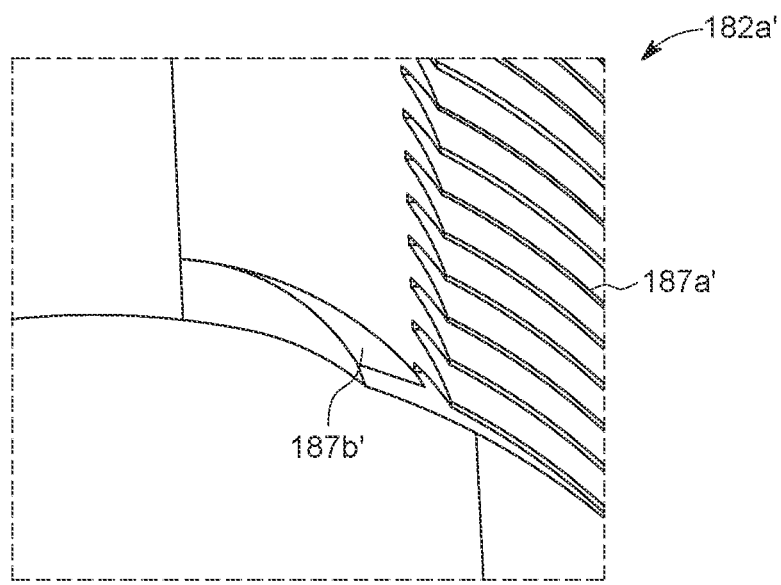
FIG. 13B is an enlarged view of a portion of the gross adjustment knob of FIG. 13A

Referring to FIG. 13A, gross correction knob 180' is illustrated with four threaded areas 182*a*' (although only two are fully visible in FIG. 13A), each threaded areas 182*a*' including a plurality of individual threads 187*a*', with the bottom-most (in the orientation of the view of FIG. 13A) thread 187*a*' including an additional guide thread 187*b*' extending therefrom. FIG. 13B is an enlarged view of one of the threaded areas 182*a*', better illustrating the guide thread 187*b*' extending from one of the threads 187*a*'. As shown in FIG. 13B, the guide thread 187*b*' may extend from an end of a thread 187*a*' and may extend farther in a circumferential direction toward the adjacent non-threaded area 182*b*' compared to the threads 187*a*' that do not include a guide thread 187*b*'. In some embodiments, the guide thread 187*b*' may be a portion of a lead-in thread at the beginning of the threaded area 182*a*', which for example may be formed with a chamfer at the end of the threaded area 182*a*'.

Figure 13C:
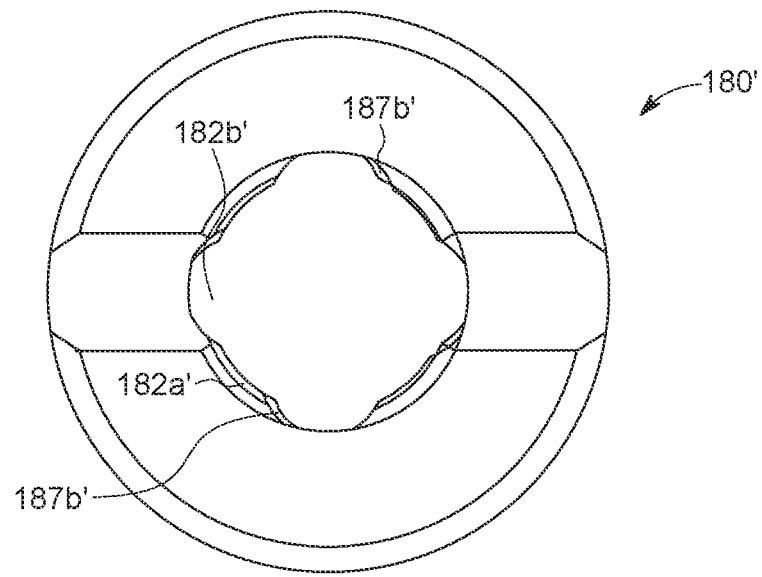
FIG. 13C is an end view of the gross adjustment knob of FIG. 13A
Figure 13D:
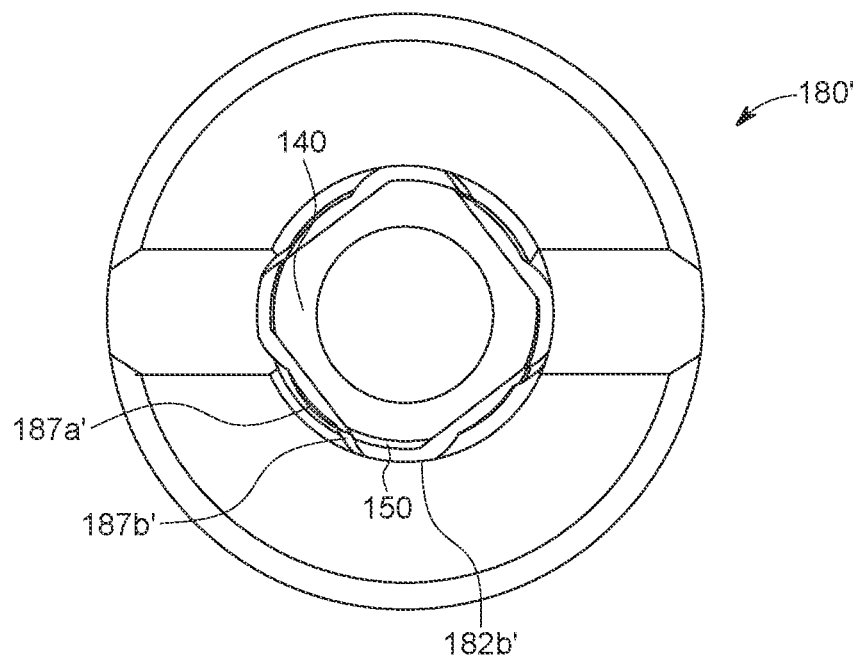
FIG. 13D is an end view of the gross adjustment knob of FIG. 13C assembled to the inner tube of FIG. 6A in an unlocked condition.

FIG. 13C is an end view of gross correction knob 180' that illustrates each threaded area 182*a*' may include a single guide thread 187*b*' extending from a corresponding thread 187*a*' in each threaded area 182*a*'. FIG. 13D illustrates the same view but also illustrates the inner tube 140 with threaded corners 150 aligned with the non-threaded areas 182*b*' in the unlocked condition. As shown in FIG. 13D, when in the unlocked condition, each guide thread 187*b*' terminates in a position immediately before engagement with (in other words very slightly spaced from) a corresponding thread 151 of a threaded corner 150 of inner tube 140. The threads 187*a*' that do not include a guide thread 187*b*' are each spaced farther away from the corresponding threads 151 of the threaded corner 150 compared to the guide thread 187*b*'. In the unlocked condition shown in FIG. 13D, the inner tube 140 is still capable of sliding axially relative to the gross correction knob 180' for quick adjustment. However, as soon as a user begins to rotate or turn the gradual correction knob 180', the guide thread 187*b*' begins to engage a trough 152 between a pair of threads 151 of the threaded corner 150. As the guide thread 187*b*' meshes with the threads 151 of the threaded corner 150 and the rotation of gradual correction knob 180' continues, the remaining threads 187*a*' are forced into alignment with the corresponding threads 151 of threaded corner 150 to reduce or eliminate the likelihood of the ends of the threads colliding and causing the "sticking" described above.

Figure 14:
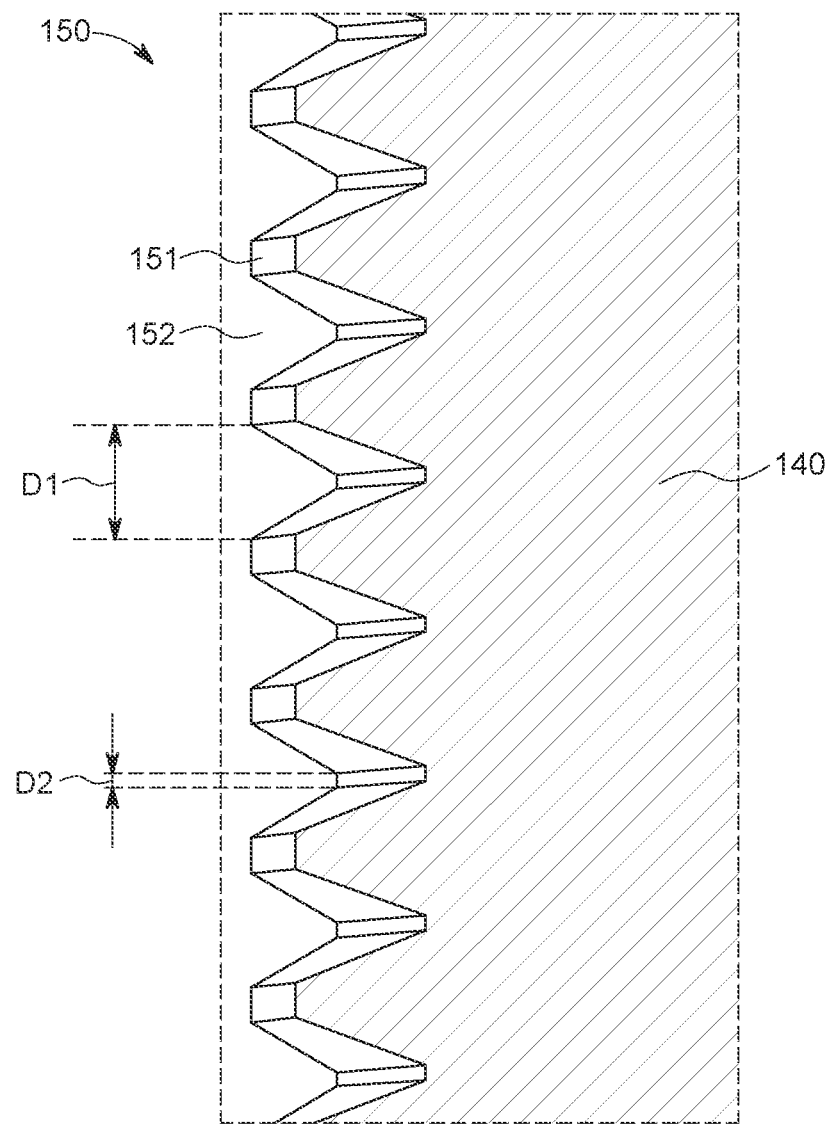
FIG. 14 is a close up view of a portion of a threaded corner of the inner tube of FIG. 6A.

FIG. 14 is a close up view of a portion of a threaded corner 150 of inner tube 140, illustrating both threads 151 and troughs 152 between adjacent peaks of the threads 151. As should be understood, the space D1 between adjacent threads 151 at the peaks of the threads 151 is relatively large, compared to the space D2 between adjacent threads 151 at the trough 152 of the threads 151. When the gradual correction knob 180' is in the unlocked condition, shown in FIG. 13D, each guide thread 187*b*' may be positioned just adjacent threaded corner 150, nearer the larger space D1 than the smaller space D2. This relative positioning may allow for a greater "landing area" for the guide thread 187*b*' to fall within to avoid the "sticking" described above. In the absence of such guide threads 187*b*', as the gradual correction knob 180' is rotated to the locked condition, the threads 187*a*' may tend to engage with threads 151 nearer the smaller space D2 than the larger space D1, potentially increasing the likelihood of threads colliding and resulting in "sticking" of the locking mechanism.

Although the main difference described above between gradual correction knob 180 and gradual correction knob 180' is the inclusion of four guide threads 187*b*', it should be understood that more or fewer guide threads may be provided, in any combination of locations. For example, guide threads 187*b*' may be provided on less than all of the groups of threaded areas 182*a*' or all of the groups of threaded areas 182*a*'. Further, in each threaded area 182*a*' that includes a guide thread 187*b*', a single guide thread 187*b*' may be provided in any particular location (e.g. at the bottom thread, top thread, or any thread in between). Still further, in each threaded area 182*a*' that include a guide thread 187*b*', more than one guide threads 187*b*' may be provided. For example, every thread of one or more threaded areas 182*a*' may include a guide thread 187*b*', or only particular threads (e.g. every other thread, every third thread, every fourth thread, etc.) may include a guide thread 187*b*'. And if multiple guide threads 187*b*' are provided within a particular threaded area 182*a*', they need not be regularly spaced relative to each other.

Figure 15A:
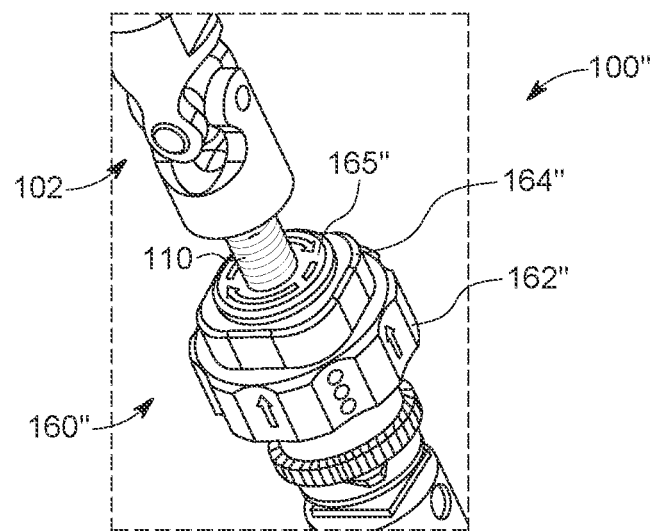
FIGS. 15A-B are perspective and cutaway views of a gradual correction knob of a strut according to an alternate aspect of the disclosure.
Figure 15B:
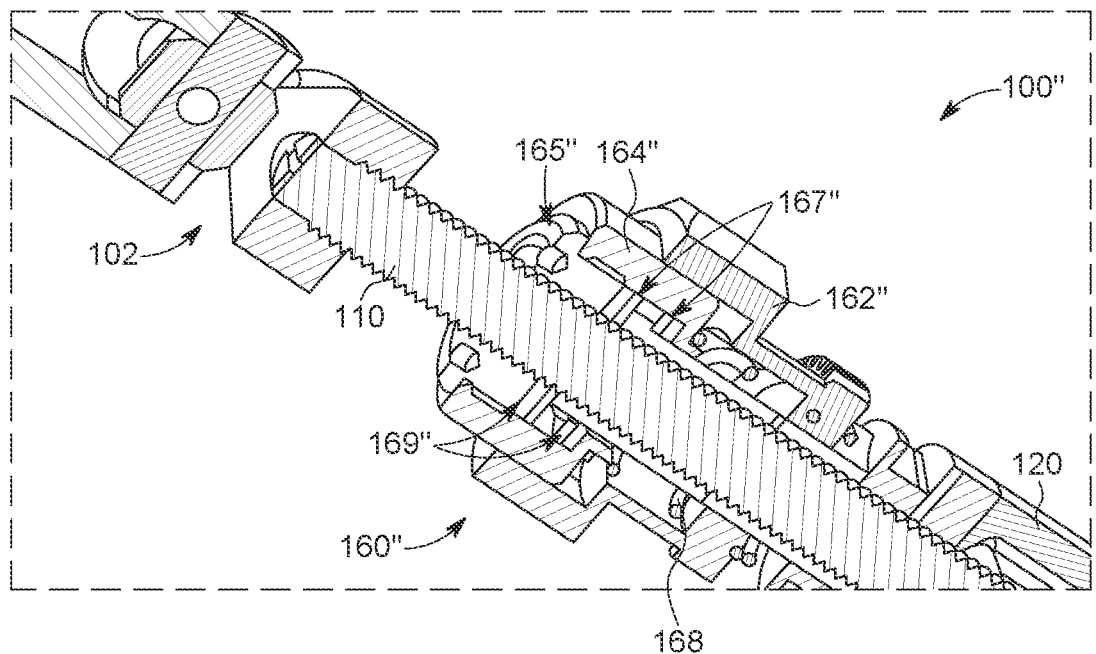

FIGS. 15A-B illustrate a strut 100" that is generally identical to strut 100 of FIG. 5, with a small number of differences. Other than the differences described herein, the description of strut 100 above applies with equal force to strut 100", and thus for brevity the similar or identical features are generally not described again here. FIGS. 15A-B focus on the end of the strut 100" having the fine adjustment knob 160". As best shown in FIG. 15A, thumb knob 162" may be substantially similar to thumb knob 162, with one difference being that the interior surface of the thumb knob 162" is substantially rectangular or square so that when the correction wheel 164" (which may have a complementary rectangular or square shape) is received within the thumb knob 162", rotation of the thumb knob 162" causes rotation of the correction wheel 164". This is in contrast to the use of pins 166 in strut 100. In addition, a number of bearings 167", 169" may be provided interior to the correction wheel 164", and may be secured via a threaded end cap 165". For example, in the illustrated embodiment of FIG. 15B, two washers 167" (e.g., stainless steel washers) may be provided on opposite sides of the lips 131 of the extensions 130, with plastic bearings 169" being positioned in contact with the washers 167" on surfaces facing away from the lips 131. Otherwise, the functionality of fine or gradual adjustment knob 160" is the same as the fine adjustment knob 160, with the adjustment knob 160" being pulled proximally against the biasing force of the spring 168 until the distal end of the adjustment knob 160" clears the flats into the unlocked condition. In this unlocked condition, the thumb knob 162" may be rotated, which causes the correction wheel 164" and threaded insert 165" to rotate relative to the threaded rod 110. As shown in FIGS. 15A-B, the distal end of the thumb knob 162" may include a gear-type structure formed integrally with the thumb knob 162". With this configuration, the adjustment knob 160" may be manually rotated as described above, or automatically adjusted via a motorized smart controller module that is snapped onto the strut 100" and into engagement with the gear structure, so that the smart controller module may cause rotation of the thumb knob 162". Suitable smart controller modules are described in greater detail in U.S. Provisional Patent Application No. 63/310,174, filed Feb. 14, 2022, and titled "Controller Module for Strut Adjustment," the disclosure of which is hereby incorporated by reference herein.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. An adjustable length strut for use in an external fixation system, the strut comprising:
   a generally hollow outer tube extending between a first end and a second end;
   an inner tube sized to fit within and translate relative to the outer tube, the inner tube extending in a length direction and having a circumferential direction, a plurality of texturized surfaces extending in the length direction of the inner tube, each of the plurality of texturized surfaces of the inner tube being spaced apart from each other in the circumferential direction of the inner tube and each circumferentially adjacent pair of texturized surfaces of the inner tube being separated by a non-texturized surface; and a first adjustment knob coupled to the second end of the outer tube, the first adjustment knob having an interior surface defining a channel, the interior surface extending in a length direction and having a circumferential direction, the inner tube passing through the channel, the interior surface having a plurality of texturized surfaces extending in the length direction of the interior surface, each of the plurality of texturized surfaces of the interior surface being spaced apart from each other in the circumferential direction of the interior surface and each circumferentially adjacent pair of texturized surfaces of the interior surface being separated by a non-texturized surface, the first adjustment knob being rotatable relative to the outer tube and the inner tube between a locked condition and an unlocked condition;

wherein (i) in the locked condition, the plurality of texturized surfaces of the inner tube engage the plurality of texturized surfaces of the interior surface of the first adjustment knob to prevent translation of the inner tube relative to the outer tube, and (ii) in the unlocked condition, the plurality of texturized surfaces of the inner tube align with the plurality of non-texturized surfaces of the interior surface of the first adjustment knob to allow translation of the inner tube relative to the outer tube, further comprising a threaded rod, wherein the inner tube is generally hollow and the threaded rod is sized to fit within the inner tube.

2. The adjustable length strut of claim 1, wherein the threaded rod passes through the first end of the outer tube.

3. The adjustable length strut of claim 1, further comprising a first joint coupled to an end of the threaded rod, and a second joint coupled to an end of the inner tube, the first joint configured to couple to a first fixation ring of the external fixation system and the second joint configured to couple to a second fixation ring of the external fixation system.

4. The adjustable length strut of claim 1, further comprising a second adjustment knob coupled to the first end of the outer tube so that the second adjustment knob is translationally fixed to the outer tube.

5. The adjustable length strut of claim 4, wherein the threaded rod passes through an aperture of the second adjustment knob.

6. The adjustable length strut of claim 5, wherein the second adjustment knob includes internal threading at the aperture configured to engage external threading of the threaded rod, so that rotation of the second adjustment knob relative to the threaded rod causes the threaded rod to translate into or out of the outer tube.

7. The adjustable length strut of claim 6, wherein the outer tube includes an outer tube slot, and the threaded rod includes a protrusion extending through the outer tube slot, the protrusion being rotatable relative to the threaded rod.

8. The adjustable length strut of claim 1, wherein an outer surface of the second end of the outer tube includes a circumferential recess.

9. The adjustable length strut of claim 8, wherein the first adjustment knob includes a first pin passing through the first adjustment knob, the first pin extending transverse the length direction of the interior surface of the first adjustment knob and being at least partially seated in the circumferential recess.

10. The adjustable length strut of claim 9, wherein the first pin prevents translational movement of the first adjustment knob relative to the outer tube.

11. The adjustable length strut of claim 9, wherein the first adjustment knob includes a second pin passing through the first adjustment knob, the second pin extending parallel to the first pin, the channel of the first adjustment knob being positioned between the first pin and the second pin, the second pin being at least partially seated in the circumferential recess.

12. The adjustable length strut of claim 1, wherein the plurality of texturized surfaces of the inner tube includes threads extending in the circumferential direction, and at least one of the threads of the inner tube includes a guide thread extending therefrom, the guide thread configured to guide the threads of the inner tube into engagement with corresponding threads of the plurality of texturized surfaces of the interior surface of the first adjustment knob as the first adjustment knob is rotated from the unlocked condition to the locked condition.

13. An adjustable length strut for use in an external fixation system, the strut comprising:

a generally hollow outer tube extending between a first end and a second end;

an inner tube sized to fit within and translate relative to the outer tube, the inner tube extending in a length direction and having a circumferential direction, a plurality of texturized surfaces extending in the length direction of the inner tube, each of the plurality of texturized surfaces of the inner tube being spaced apart from each other in the circumferential direction of the inner tube and each circumferentially adjacent pair of texturized surfaces of the inner tube being separated by a non-texturized surface; and a first adjustment knob coupled to the second end of the outer tube, the first adjustment knob having an interior surface defining a channel, the interior surface extending in a length direction and having a circumferential direction, the inner tube passing through the channel, the interior surface having a plurality of texturized surfaces extending in the length direction of the interior surface, each of the plurality of texturized surfaces of the interior surface being spaced apart from each other in the circumferential direction of the interior surface and each circumferentially adjacent pair of texturized surfaces of the interior surface being separated by a non-texturized surface, the first adjustment knob being rotatable relative to the outer tube and the inner tube between a locked condition and an unlocked condition;

wherein (i) in the locked condition, the plurality of texturized surfaces of the inner tube engage the plurality of texturized surfaces of the interior surface of the first adjustment knob to prevent translation of the inner tube relative to the outer tube, and (ii) in the unlocked condition, the plurality of texturized surfaces of the inner tube align with the plurality of non-texturized surfaces of the interior surface of the first adjustment knob to allow translation of the inner tube relative to the outer tube, further comprising a quick-release pin and spring both at least partially received within the first adjustment knob, the quick-release pin including a shoulder extending toward the second end of the outer tube.

14. The adjustable length strut of claim 13, wherein the second end of the outer tube includes a first detent circumferentially spaced from a second detent.

15. The adjustable length strut of claim 14, wherein when the shoulder of the quick-release pin is received within the first detent, the first adjustment knob is in the locked condition, and when the shoulder of the quick-release pin is received within the second detent, the first adjustment knob is in the unlocked condition.

16. The adjustable length strut of claim 15, wherein the spring biases the shoulder into the first detent when the first adjustment knob is in the locked condition, and the spring biases the shoulder into the second detent when the first adjustment knob is in the unlocked condition, the spring bias tending to prevent rotation of the first adjustment knob relative to the outer tube in the absence of applied forces.

17. The adjustable length strut of claim 15, wherein the second end of the outer tube includes an arcuate recess positioned generally diametrically opposed to the first detent and the second detent.

18. The adjustable length strut of claim 17, further comprising a rotation limiting pin at least partially received within the first adjustment knob, a terminal end of the rotation limiting pin extending into the arcuate recess.

19. The adjustable length strut of claim 18, wherein the arcuate recess is bounded by a first limiting surface and a second limiting surface, and contact between the rotation limiting pin and the first and second limiting surfaces define the extent to which the first adjustment knob is capable of rotation relative to the outer tube.

20. The adjustable length strut of claim 19, wherein when the terminal end of the rotation limiting pin is in contact with the first limiting surface, the shoulder of the quick-release pin is received within the first detent and the first adjustment knob is in the locked condition, and when the terminal end of the rotation limiting pin is in contact with the second limiting surface, the shoulder of the quick-release pin is received within the second detent and the first adjustment knob is in the unlocked condition.

\* \* \* \* \*